United States Patent
Spruit et al.

(10) Patent No.: US 9,750,589 B2
(45) Date of Patent: Sep. 5, 2017

(54) PLAQUE DETECTION USING A STREAM PROBE

(71) Applicant: KONINKLIJKE PHILIPS N.V., Eindhoven (NL)

(72) Inventors: Johannes Hendrikus Maria Spruit, Waalre (NL); Mark Thomas Johnson, Arendonk (BE); Menno Willem Jose Prins, Rosmalen (NL); Okke Ouweltjes, Veldhoven (NL); Steven Charles Deane, Cambridge (GB); Edgar Martinus Van Gool, Veghel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/650,882

(22) PCT Filed: Dec. 20, 2013

(86) PCT No.: PCT/IB2013/061188
§ 371 (c)(1),
(2) Date: Jun. 10, 2015

(87) PCT Pub. No.: WO2014/097241
PCT Pub. Date: Jun. 26, 2014

(65) Prior Publication Data
US 2015/0327966 A1 Nov. 19, 2015

Related U.S. Application Data

(60) Provisional application No. 61/746,361, filed on Dec. 27, 2012, provisional application No. 61/740,904, filed on Dec. 21, 2012.

(51) Int. Cl.
*A61C 1/00* (2006.01)
*A61M 37/00* (2006.01)
(Continued)

(52) U.S. Cl.
CPC .......... *A61C 19/04* (2013.01); *A46B 15/0036* (2013.01); *A61B 5/0013* (2013.01);
(Continued)

(58) Field of Classification Search
USPC ............................................. 433/27; 604/154
See application file for complete search history.

(56) References Cited

U.S. PATENT DOCUMENTS

| 4,481,833 A | 11/1984 | Bajek |
| 4,551,292 A | 11/1985 | Fletcher et al. |

(Continued)

FOREIGN PATENT DOCUMENTS

| CN | 102427863 A | 4/2012 |
| JP | 2013017603 A | 1/2013 |

(Continued)

OTHER PUBLICATIONS

Klopfenstein et al: "Ultrasonic Aspirator Tip Variations:Instrumentation Assessment"; Barrow Quarterly—vol. 20, No. 3, 2004, 4 Page Document.

*Primary Examiner* — Nicole F Johnson

(57) ABSTRACT

An apparatus is configured such that passage of a fluid through an open port of a distal probe tip enables detection of a substance that may be present on a surface, e.g., a surface of a tooth, based on measurement of a signal correlating to a substance at least partially obstructing the passage of fluid through the open port. The apparatus includes a proximal pump portion and at least one distal probe portion configured to be immersed in another fluid, e.g., water in toothpaste foam. A corresponding system includes one or two such apparatuses. A method of detecting the presence of a substance on a surface includes probing an interaction zone for at least partial obstruction of flow of the fluid through the distal probe tip. The distal probe tip may have a structural configuration for preventing blocking of (Continued)

the open port. The distal probe tip may also have a non-uniform wear profile. The at least one distal probe portion may include two or multiple components to improve performance and reliability.

9 Claims, 16 Drawing Sheets

(51) Int. Cl.
  *A61C 19/04* (2006.01)
  *A61C 17/22* (2006.01)
  *G01N 7/00* (2006.01)
  *A61B 5/00* (2006.01)
  *A46B 15/00* (2006.01)

(52) U.S. Cl.
  CPC .......... *A61B 5/0088* (2013.01); *A61B 5/4547* (2013.01); *A61B 5/4552* (2013.01); *A61B 5/6891* (2013.01); *A61B 5/742* (2013.01); *A61B 5/7405* (2013.01); *A61B 5/746* (2013.01); *A61C 17/22* (2013.01); *A61C 17/227* (2013.01); *G01N 7/00* (2013.01); *A61B 2562/0233* (2013.01); *A61B 2562/0247* (2013.01); *A61B 2562/0261* (2013.01); *A61B 2576/02* (2013.01)

(56) References Cited

U.S. PATENT DOCUMENTS

| | | | |
|---|---|---|---|
| 4,829,836 A | 5/1989 | Daverio et al. | |
| 5,354,999 A | 10/1994 | Neff | |
| 6,485,465 B2* | 11/2002 | Moberg | A61M 5/1456 417/18 |
| 6,712,797 B1 | 3/2004 | Southern, Jr. | |
| 6,862,771 B1 | 3/2005 | Muller | |
| 2003/0143510 A1 | 7/2003 | Berube-Lauziere et al. | |
| 2005/0171467 A1 | 8/2005 | Landman | |
| 2006/0014118 A1 | 1/2006 | Utama | |
| 2007/0157404 A1 | 7/2007 | Brewer et al. | |
| 2008/0060148 A1* | 3/2008 | Pinyayev | A61B 5/0088 15/22.1 |
| 2011/0117517 A1 | 5/2011 | Bergheim et al. | |
| 2012/0065580 A1 | 3/2012 | Gerg et al. | |
| 2012/0276499 A1 | 11/2012 | Devery et al. | |
| 2012/0295216 A1* | 11/2012 | Dykes | A61C 19/04 433/27 |
| 2013/0023918 A1 | 1/2013 | Morlet et al. | |

FOREIGN PATENT DOCUMENTS

WO 2010134049 A1 11/2010
WO 2011038949 A1 4/2011

\* cited by examiner

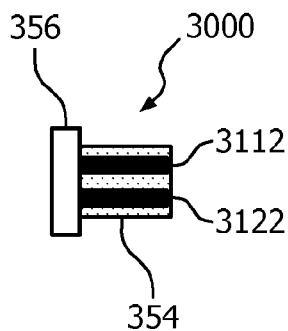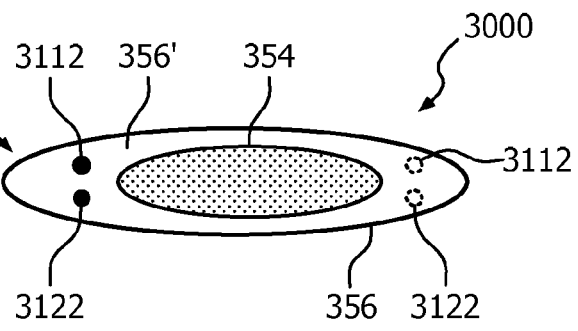
FIG. 16     FIG. 14
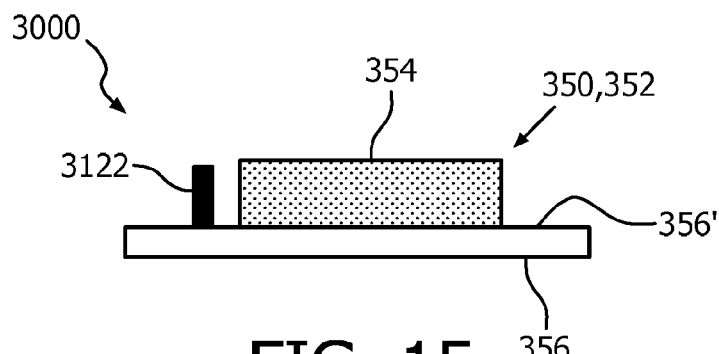
FIG. 15
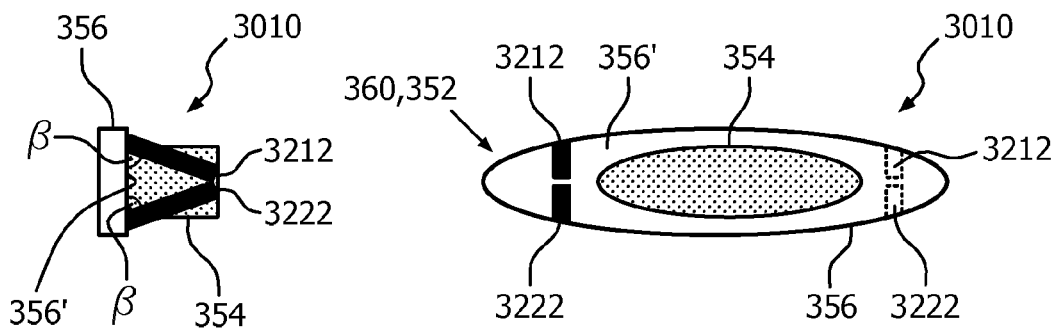
FIG. 19     FIG. 17
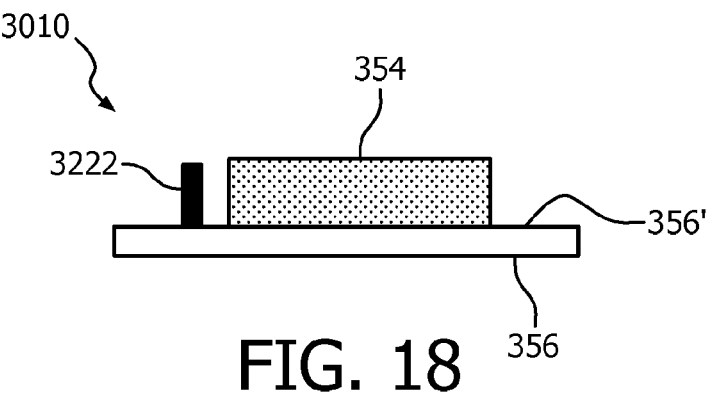
FIG. 18

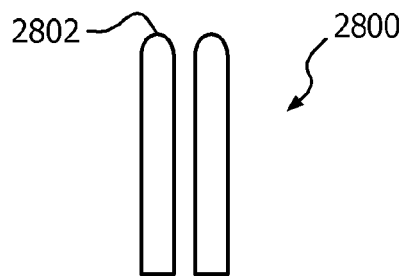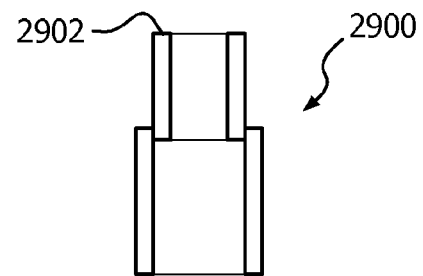
FIG. 28  FIG. 29
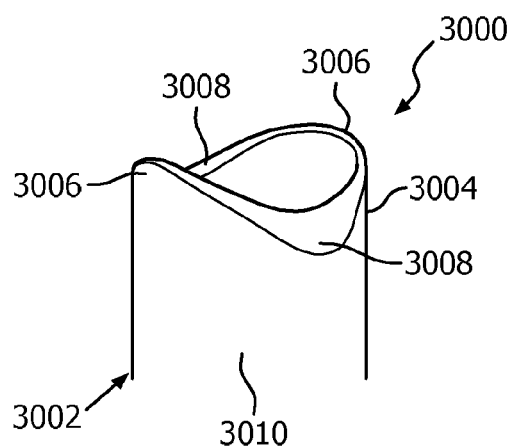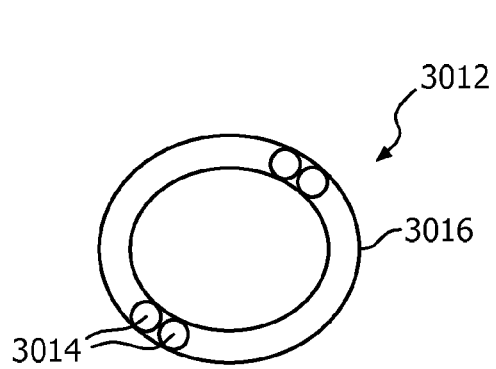
FIG. 30  FIG. 31
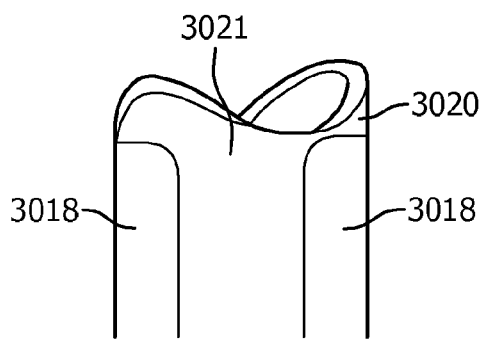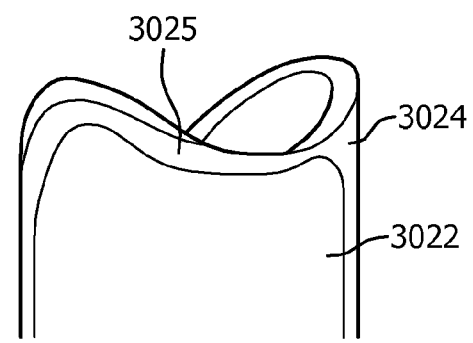
FIG. 32  FIG. 33

PLAQUE DETECTION USING A STREAM PROBE

CROSS-REFERENCE TO PRIOR APPLICATIONS

This application is the U.S. National Phase application under 35 U.S.C. §371 of International Application No. PCT/IB2013/061188, filed on Dec. 20, 2013, which claims the benefit of U.S. Provisional Patent Application No.61/746,361, filed on Dec. 27, 2012 and U.S. Provisional Patent Application No. 61/740,904, filed on Dec. 21, 2012. These applications are hereby incorporated by reference herein.

TECHNICAL FIELD

The present disclosure relates to apparatuses used for detecting the state of a surface. More particularly, the present disclosure relates to a stream probe that is utilized to detect the state of a dental surface.

BACKGROUND OF THE INVENTION

Caries or periodontal diseases are thought to be infectious diseases caused by bacteria present in dental plaques. Removal of dental plaques is highly important for the health of oral cavities. Dental plaques, however, are not easy to identify by the naked eye. A variety of plaque detection apparatuses have been produced to aid in the detection of dental plaque and/or caries.

Most of the dental plaque detection apparatuses are configured for use by trained professionals and make use of the fact that the visible luminescence spectra from dental plaque (and/or caries) and non-decayed regions of a tooth are substantially different. Some dental plaque detection apparatuses are configured for use by consumers (most of whom are, typically, not trained dental professionals) in their own homes in helping consumers achieve good oral hygiene.

For example, one known type of dental plaque apparatus utilizes irradiated light to illuminate tooth material and gums to identify areas infected by biofilms and areas of dental plaque. This type of plaque detection apparatus may utilize a monochromatic excitation light and may be configured to detect fluorescent light in 2 bands 440-470 nm (e.g., blue light) and 560-640 nm (e.g., red light); the intensities are subtracted to reveal the dental plaque and/or caries regions.

While the aforementioned dental plaque apparatus are suitable for their intended use, they exhibit one or more shortcomings. Specifically, it is known that each area of the eye absorbs different wavelengths of light and, if too much light is absorbed by the eye, the eye may be damaged. As can be appreciated, to avoid possible eye injury, it is imperative that a user not switch on the plaque detection apparatus until the plaque detection apparatus is appropriately placed inside the mouth. The aforementioned devices, however, are not configured to automatically detect when the plaque detection apparatus are placed inside the mouth. As a result thereof, potentially harmful radiation that could damage the eyes, or cause uncomfortable glare if exposed to the eyes, may result if proper handling precautions are not followed, e.g., consumer misuse. Furthermore, this technique is especially suitable to detect old plaque; a distinction between teeth fluorescence and young (1 day old) plaque fluorescence is not made.

SUMMARY OF THE INVENTION

It is an object of the invention to provide an improved detection of a substance (e.g. plaque) on a surface (e.g. a dental surface).

Accordingly, an aspect of the present disclosure includes an apparatus for detecting the presence of a substance on a surface. The apparatus includes a proximal body portion comprising a proximal pump (e.g., syringe) portion and a proximal probe portion and at least one distal probe portion configured to be immersed in a first fluid. The proximal pump portion and the distal probe portion are in fluid communication with one another. The distal probe portion defines a distal tip having an open port to enable the passage of a second fluid (e.g. a gas or a liquid) there through. The apparatus is configured such that passage of the second fluid through the distal tip enables detection of a substance that may be present on the surface based on measurement of a signal correlating to a substance at least partially obstructing the passage of fluid through the open port of the distal tip.

In one aspect, the signal may be a pressure signal and the detection apparatus further includes a pressure sensor configured and disposed to detect the pressure signal. The proximal pump portion may include the pressure sensor.

In one aspect, the apparatus may further include a pressure sensing portion disposed between the proximal pump portion and the distal probe portion wherein the pressure sensor is disposed in fluid communication with the pressure sensing portion to detect the pressure signal. The proximal pump portion, the pressure sensing portion and the distal probe portion may each define internal volumes summing to a total volume of the detection apparatus such that the detection apparatus forms an acoustical low pass filter.

In another aspect, the proximal pump portion may include a moveable plunger disposed therewithin and configured and disposed such that the moveable plunger is reciprocally moveable away from a proximal end of the proximal pump portion towards a distal end of the proximal pump portion. The movement of the plunger induces thereby a volumetric or mass flow in the distal probe portion or wherein the proximal pump portion comprises a moveable diaphragm, the movement of the diaphragm inducing thereby a change in volumetric or mass flow in the distal probe portion.

The apparatus may further include a controller. The controller may process pressure readings sensed by the pressure sensor and determine whether the pressure readings are indicative of a substance obstructing the passage of fluid through the open port of the distal tip. The substance may be dental plaque.

In yet another aspect of the apparatus, the signal represents strain of the probe portion. The detection apparatus may further include a strain gauge configured and disposed on the distal probe portion to enable the strain gauge to detect and measure the signal representing strain of the probe portion.

In one aspect, the distal tip having an open port may be chamfered at an angle such that passage of the second fluid through the distal tip is enabled when the distal tip touches the surface. The angle of the chamfer of the open port may be such that passage of the second fluid through the distal tip is at least partially obstructed when the distal tip touches the surface and a substance at least partially obstructs the passage of fluid through the open port of the distal tip. Other structural configurations for the distal tip of the distal probe portion are contemplated herein for preventing blockage or obstruction of the passage of fluid through the open port of the distal tip. These structural configurations also prevent false positives by ensuring that on a flat surface a flow escapes from the distal tip.

Yet another aspect of the present disclosure includes a proximal body portion that includes a pump portion, a proximal probe portion wherein the pump portion and the proximal probe portion are in fluid communication with one another, and a connector wherein the proximal probe portion can be connected via the connector to a distal probe portion of a distal probe portion of the detection apparatus to establish fluid communication between the proximal probe portion and the distal probe portion. The detection apparatus includes a distal probe portion configured to be immersed in a first fluid. The distal probe portion defines a distal tip having an open port to enable the passage of a second fluid therethrough. The apparatus is configured such that passage of the second fluid through the distal tip enables detection of a substance that may be present on the surface based on measurement of a signal, correlating to a substance at least partially obstructing the passage of fluid through the open port of the distal tip.

Yet another aspect of the present disclosure includes a system for detecting the presence of a substance on a surface. The system includes a first detection apparatus as described above and at least a second detection configured in the manner as the first detection apparatus as described above.

Yet another aspect of the present disclosure includes a method of detecting the presence of a substance on a surface that includes, via a stream probe tubular member or stream probe defining a proximal end and an interior channel that includes a distal probe tip having an open port enabling the passage of a fluid medium therethrough, disposing the probe tip in proximity to a surface and such that the stream probe tubular member is immersed in a first fluid medium, causing a second fluid medium to flow through the interior channel and the distal probe tip and causing the distal probe tip to touch the surface in an interaction zone occurring in the first fluid medium, and probing the properties of the interaction zone via detection of at least partial obstruction of flow of the second fluid medium through the interior channel or the distal probe tip or combinations thereof.

Yet another aspect of the present disclosure includes a method of detecting the presence of a substance on a surface that includes, via at least two stream probe tubular members or stream probes each defining a proximal end and an interior channel that includes a distal probe tip having an open port enabling the passage of a fluid medium therethrough, disposing the two probe tips in proximity to a surface and such that the two stream probe tubular members or stream probes are immersed in a first fluid medium, causing a second fluid medium to flow through the interior channels and the distal probe tips and causing the distal probe tips to touch the surface in an interaction zone occurring in the first fluid medium, and probing the properties of the interaction zone via detection of at least partial obstruction of flow of the second fluid medium through the interior channels or the distal probe tips or combinations thereof.

In one aspect, the detection of at least partial obstruction of flow of the second fluid medium through the interior channels and the distal probe tips may include detection of a difference between a pressure signal detected in one of the two stream probe tubular members and another one of the two stream probe tubular members.

In another aspect, the detection of at least partial obstruction of flow of the second fluid medium through the interior channels and the distal probe tips may include detection of a difference between a strain signal detected in one of the two stream probe tubular members and another one of the two stream probe tubular members.

In yet a another aspect, the distal tip has an open port that may be chamfered at an angle such that the step of causing a second fluid medium to flow through the interior channels and the distal probe tips is enabled when the distal tip touches the surface and the second fluid medium is enabled to flow through the chamfered open port. Other structural configurations for the distal tip of the distal probe portion are contemplated herein for preventing blockage or obstruction of the passage of fluid through the open port of the distal tip. These structural configurations also prevent false positives by ensuring that on a flat surface a flow escapes from the distal tip.

In a further aspect, the step of detecting at least partial obstruction of flow of the second fluid medium through at least one of the interior channels and the distal probe tips is enabled via the angle of the chamfer of the open port being such that passage of the second fluid through the distal tip is at least partially obstructed when the distal tip touches the surface and a substance at least partially obstructs the passage of the second fluid medium through the open port of the distal tip.

In one aspect, the probing of the properties of the interaction zone may include measuring a property of dental plaque derived from the surface in the interaction zone.

In still another aspect, the causing a second fluid medium to flow through the interior channels and the distal probe tips may be performed either by causing the second fluid medium to flow distally from the proximal ends of the at least two stream probe tubular members through the distal probe tips or by causing the second fluid medium to flow proximally from the distal probe tips through the interior channels towards the proximal ends of the stream probe tubular members.

The present disclosure describes a method of probing a dental surface by recording the outflow properties of a fluid medium through a probe tip. The properties of the fluid outflowing from the probe tip can for example be measured by recording the pressure of the fluid medium as a function of time. The release properties of fluid, including bubbles, from the tip-surface region can characterize the dental surface and/or the viscoelastic properties of dental material present at the probe tip. The fluid, including bubbles, may also improve the plaque removal rate of the tooth brush.

Novel features of exemplary embodiments of the present disclosure are:

(a) a fluid medium is brought in contact with a surface at a probe tip, generating an interaction zone between the tip and the surface; and (b) the shape and/or dynamics of the medium in the interaction zone depend on the properties of the surface and/or on materials derived from the surface; and (c) the pressure and/or shape and/or dynamics of the medium in the interaction zone are detected.

A determination is made by a controller as to whether a level of plaque is detected at a particular dental surface of a tooth that exceeds a predetermined maximum acceptable or permissible level of plaque.

If a negative detection is made, a signal is transmitted to the user of the electric toothbrush having an integrated stream probe plaque detection system to advance the brush to an adjacent tooth or other teeth.

Alternatively, if a positive detection is made, a signal is transmitted to the user of the electric toothbrush having an integrated stream probe plaque detection system to continue brushing the particular tooth.

Accordingly, the embodiments of the present disclosure relate to an apparatus that is configured such that passage of a fluid through an open port of a distal tip enables detection of a substance that may be present on a surface, e.g., a surface of a tooth, based on measurement of a signal correlating to a substance at least partially obstructing the passage of fluid through the open port. The apparatus includes a proximal pump portion and at least one distal probe portion configured to be immersed in another fluid. The apparatus may be included within a corresponding system that includes at least two apparatuses. A method includes probing an interaction zone for at least partial obstruction of flow.

In one exemplary embodiment, the first fluid may also pass through the open port of the distal tip of the distal probe portion, e. g., when the pressure within the distal probe portion is below ambient pressure.

According to aspects of the present disclosure, the distal tip of the distal probe portion may include a structural configuration having a wear profile which is non-uniform around the circumference of the open port. The non-uniform wear profile ensures that the distal tip maintains its shape to a sufficient extent over a longer period of time. In one aspect of the present disclosure, a structural configuration of the distal tip includes at least two zones with different wear characteristics during brushing. The zones with different wear characteristics are alternatively placed over the circumference of the distal probe portion, e.g., alternating wear characteristics yielding a relatively high wear, low wear, high wear, and low wear.

According to further aspects of the present disclosure, the distal probe portion of the stream probes of the various embodiments described herein have structural configurations which include two or multiple segments or components to improve performance and reliability.

These and other aspects of the present disclosure will be apparent from and elucidated with reference to the embodiment(s) described hereinafter.

BRIEF DESCRIPTION OF THE DRAWINGS

The aspects of the present disclosure may be better understood with reference to the following figures. The components in the figures are not necessarily to scale, emphasis instead being placed upon clearly illustrating the principles of the disclosure. Moreover, in the figures, like reference numerals designate corresponding parts throughout the several views.

In the figures:

FIG. 14 illustrates an alternate exemplary embodiment of the brush of FIG. 10 that includes multiple stream probes on the brush that includes the base of the brush such as according to the embodiment of a stream probe according to FIG. 13;

FIG. 15 illustrates another view of the brush of FIG. 14;

FIG. 16 illustrates still another view of the brush of FIG. 14;

FIG. 17 illustrates another alternate exemplary embodiment of the brush of FIG. 10 that includes multiple stream probes on the brush that includes the base of the brush;

FIG. 18 illustrates another view of the brush of FIG. 17;

FIG. 19 illustrates still another view of the brush of FIG. 17;

FIG. 24A illustrates a castle-shape embodiment, and FIG. 24B illustrates a round-shape embodiment;

FIG. 28 illustrates an embodiment of another structural configuration of the distal tip according to the present disclosure which includes a rounded wall; and FIG. 29 illustrates an embodiment of yet another structural configuration of the distal tip according to the present disclosure which includes at least one bumper element extending from the distal tip;

FIG. 30 illustrates a stream probe tip or distal tip having a non-uniform wear profile;

FIG. 31 illustrates a cross-section of a stream probe; where a first material is embedded into a second material to create a distal tip for the stream probe having a non-uniform wear profile according to an embodiment of the present disclosure;

FIG. 32 illustrates a configuration of the embodiment shown by FIG. 31 in which layers of a material are placed at strategic positions around a tube of another material to create a non-uniform wear profile;

FIG. 33 illustrates another configuration of the embodiment shown by FIG. 31 in which layers of a material are placed entirely around a tube of another material to create a non-uniform wear profile;

DETAILED DESCRIPTION OF EMBODIMENTS

The present disclosure describes various embodiments of systems, devices, and methods related to assisting users to clean their teeth, in particular by informing users if they are indeed removing plaque from their teeth and if they have fully removed the plaque, providing both reassurance and coaching them into good habits. In one exemplary embodiment, the information is provided in real time during brushing, as otherwise consumer acceptance is likely to be low. For example, it is useful if a toothbrush gives the user a signal when the position at which they are brushing is clean, so they can move to the next tooth. This may reduce their brushing time, but will also lead to a better, more conscious brushing routine.

A particular goal of utilization of the exemplary embodiments of the present disclosure is to be able to detect plaque within a vibrating brush system surrounded with toothpaste foam, e.g., a Philips Sonicare toothbrush. The detection system should provide contrast between a surface with the thicker, removable plaque layers, and a more clean pellicle/calculus/thin plaque/tooth surface.

Figure 1:
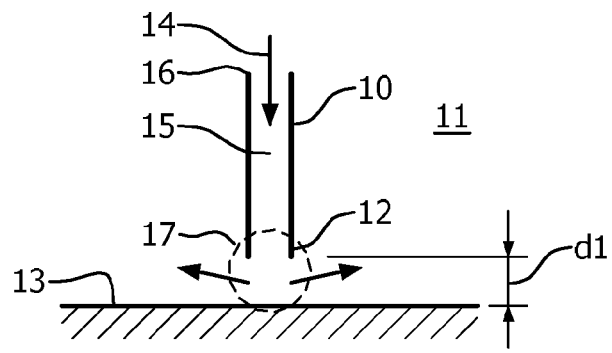
FIG. 1 illustrates the general principle of a stream probe impacting a dental surface in accordance with the present disclosure.

FIG. 1 illustrates a method of detecting the presence of a substance on a surface, e.g., a substance such as dental plaque on a surface such as tooth enamel, using a stream probe 10 according to one exemplary embodiment of the present disclosure. The stream probe 10, exemplarily illustrated as a cylindrical tube member, defines a proximal end 16, an interior channel 15 and a distal probe tip 12. The interior channel 15 contains a fluid medium 14, e.g. a gas or a liquid. The probe tip 12 is placed in the proximity of a surface 13, e.g. a dental surface. The probe 10 is immersed in a fluid medium 11, e.g. an aqueous solution such as a dental cleaning solution. Probe fluid medium 14 flows through the probe channel 15 and touches surface 13 in interaction zone 17. The properties of the interaction zone 17 are probed via the outflow of probe medium 14.

As described in more detail below with respect to FIG. 10, an apparatus or instrument for detecting the presence of a substance on a surface, such as a dental cleaning instrument including an electric toothbrush having an integrated stream probe plaque detection system, is configured such that fluid medium 14 is brought in contact with surface 13, e.g. a dental surface, at probe tip 12, generating interaction zone 17 between distal tip 12 and surface 13.

The shape and/or dynamics of the medium 14 in the interaction zone 17 depend on the properties of the surface 13 and/or on materials derived from the surface 13, the pressure and/or shape and/or dynamics of the medium 14 in the interaction zone 17 are detected and a determination is made by a controller as to whether a predetermined maximum acceptable level of plaque is detected at the particular dental surface 13, as described in more detail below with respect to FIG. 10.

More particularly, when medium 14 is a gas 30 (see FIG. 2), then a gas meniscus will appear at the tip 12 and will become in contact with surface 13. The shape and dynamics of the gas at the tip will depend on the properties of the probe tip 12 (e.g. tip material, surface energy, shape, diameter, roughness), properties of solution 11 (e.g. materials composition), properties of medium 14 (e.g. pressure, flow speed), and properties of surface 13 (e.g. viscoelastic properties, surface tension) and/or on materials derived from the surface 13 (viscoelastic properties, adherence to surface, texture etc.).

Figure 2:
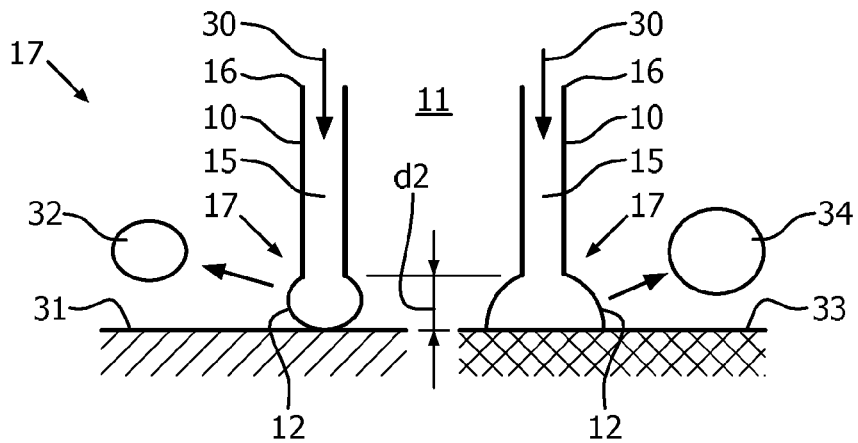
FIG. 2 illustrates the effect of surface tension on a less hydrophilic surface and on a more hydrophilic surface for a stream probe impacting a dental surface in accordance with one exemplary embodiment of the present disclosure.

FIG. 2 illustrates the influence of surface tension. In the case of a surface with a high surface energy or a strongly hydrated surface, e.g. a hydrophilic surface 31 such as the surface of plaque as illustrated in the left photograph, the gas 30 will not easily displace the aqueous medium 11 from the surface 31 near the interaction zone 17.

In the case of a surface with a low surface energy or a less hydrated surface, e.g. a less hydrophilic surface 33 such as the enamel surface of a tooth as illustrated in the right photograph, the gas 30 more easily displaces the aqueous medium 11 from the surface 33. The properties (shape, pressure, release rate, etc) of bubbles 32 and 34 depend on the surface tension of the dental surface 31 or 33. This is referred to as the bubble method. That is, the stream probe or distal probe portion 10 is configured such that passage of the second fluid such as the gas 30 through the distal tip 12 enables detection of a substance that may be present on the surface 31 or 33 based on measurement of a signal correlating to, in proximity to the surface 31 or 33, one or more bubbles 32 or 34 generated by the second fluid such as the gas 30 in the first fluid such as the aqueous medium 11.

Figure 3:
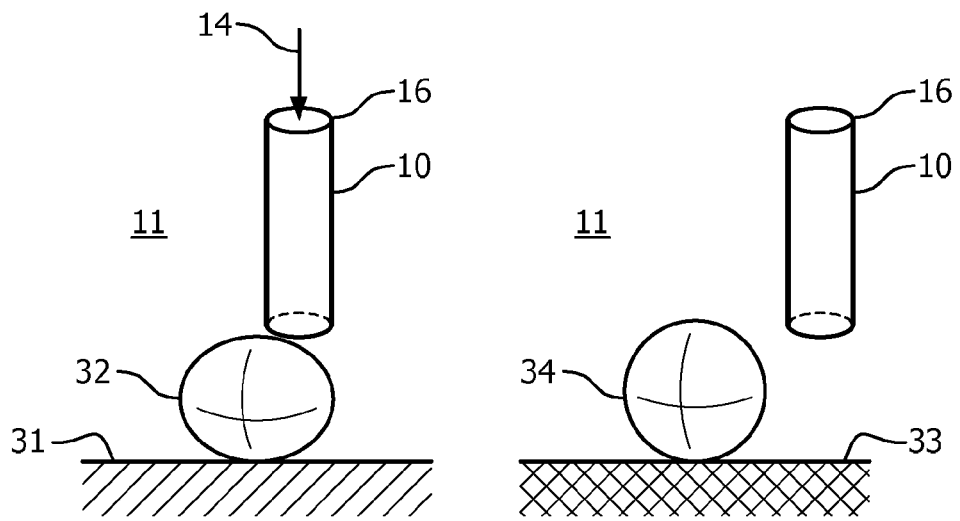
FIG. 3 illustrates left and right photographs of air bubbles from a needle in water touching a plaque surface on the left and an enamel surface on the right in accordance with one exemplary embodiment of the present disclosure.

FIG. 3 illustrates photographs of such types of air bubbles 32 and 34 from stream probe 10 under aqueous solution 11, e.g., water. As illustrated in the left photograph, an air bubble 32 does not stick on a wet plaque layer 31, while, as illustrated in the right photograph, air bubble 34 does stick on enamel surface 33, showing that the plaque layer 31 is more hydrophilic as compared to enamel surface 33.

Figure 4A:
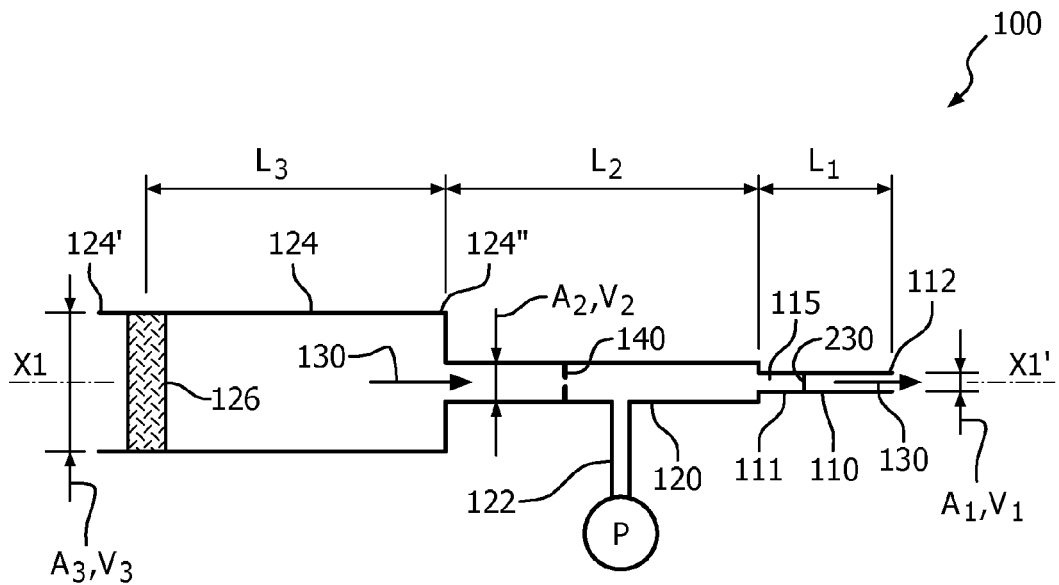
FIG. 4A illustrates one exemplary embodiment of the present disclosure of a stream probe having a pump portion supplying a continuous stream of gas via a tube to a probe tip while measuring the internal tube pressure.
Figure 4B:
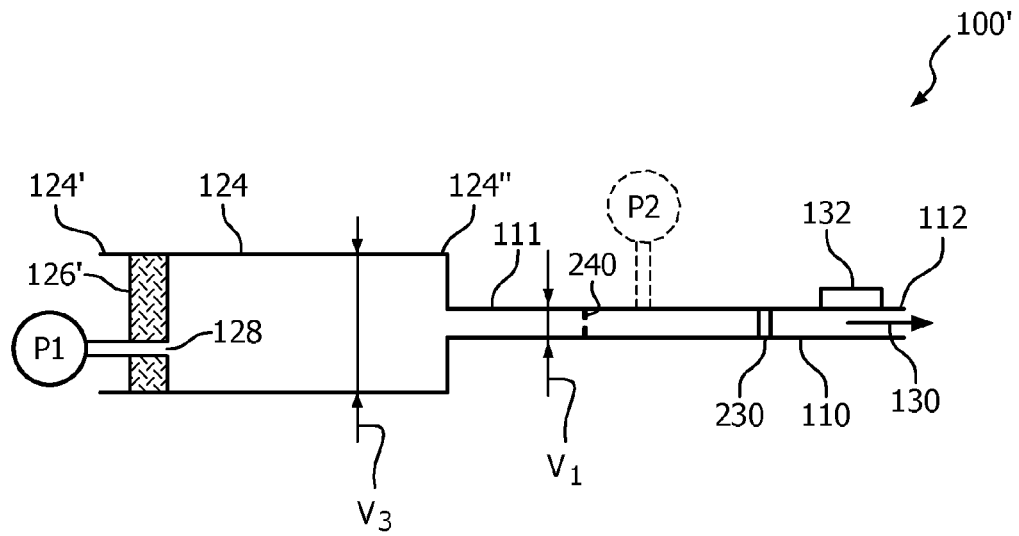
FIG. 4B illustrates another exemplary embodiment of the stream probe of FIG. 4A having one exemplary embodiment of a pump portion supplying a continuous stream of gas via a tube to a probe tip while measuring the internal pump pressure.
Figure 4C:
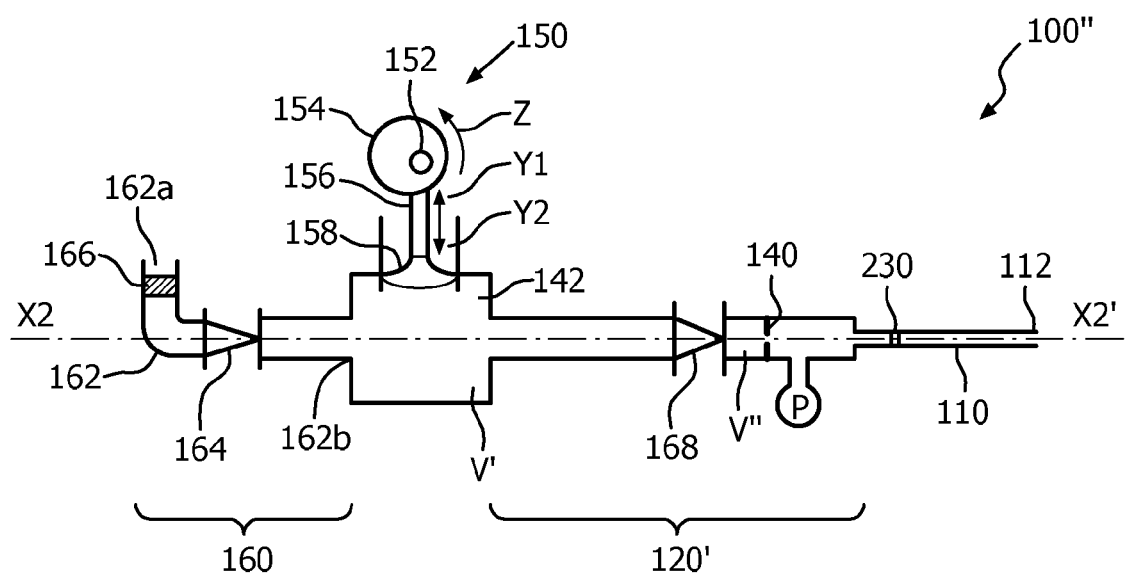
FIG. 4C illustrates another exemplary embodiment of the stream probe of FIGS. 4A and 4B having another exemplary embodiment of a pump portion supplying a generally continuous stream of gas via a tube to a probe tip while measuring the internal pump pressure.

FIGS. 4A, 4B and 4C each illustrate a detection apparatus or instrument for detecting the presence of a substance on a surface according to exemplary embodiments of the present disclosure, wherein the detection apparatus is exemplified by a stream probe that includes a parameter sensor to demonstrate the principle of plaque detection by parameter sensing and measurement. As defined herein, a parameter sensor includes a pressure sensor or a strain sensor or a flow sensor, or combinations thereof, which sense a physical measurement represented by a signal that is indicative of blockage of flow in the stream probe which may, in turn, be indicative of plaque or other substance blocking flow in the stream probe. A flow sensor which measures differential pressure or flow of heat from a wire which has been heated above ambient temperature are flow sensors or other means known or to be conceived for pressure, strain or flow or other measurement, including chemical or biological measurements, are included within the definition of a parameter sensor which sense a physical measurement represented by a signal that is indicative of blockage of flow in the stream probe which may be indicative of plaque or other substance blocking flow in the stream probe. For simplicity, for the purposes of description, the parameter sensor or sensors are exemplified by one or more pressure sensors. Although the locations for the parameter sensors illustrated in the figures are intended to apply generically to each different type of parameter, those skilled in the art will recognize that the location of the parameter sensor may be adjusted, if necessary, from the location or locations shown in the drawings, depending on the specific type of parameter sensor or sensors being employed. The embodiments are not limited in this context.

More particularly, in FIG. 4A, a stream probe 100 includes a proximal pump portion 124 such as a tubular syringe portion as shown, a central parameter sensing portion 120, exemplarily having a tubular configuration as shown, and a distal probe portion 110, also exemplarily having a tubular configuration as shown, defining a distal probe tip 112. The distal tubular probe portion 110 defines a first length L1 and a first cross-sectional area A1, the central parameter sensing tubular portion 120 defines a second length L2 and a second cross-sectional area A2, while the proximal tubular syringe portion 124 defines a third length L3 and a third cross-sectional area A3. The proximal tubular syringe portion 124 includes, e.g., in the exemplary embodiment of FIG. 4A, reciprocally movable plunger 126 initially disposed in the vicinity of proximal end 124'.

A continuous fluid steam 130 of air is supplied by the plunger 126 through the central parameter sensing portion tubular portion 120 to the probe tip 112 when the plunger moves longitudinally along the length L3 at a constant velocity and away from the proximal end 124'. When the fluid stream 130 is a gas, a continuous stream 130 of gas is supplied through the plunger 126 (such as via an aperture 128 in the plunger 126 (see plunger 126' in FIG. 4B) or from a branch connection 122 connecting to the central parameter sensing tubular portion 120 to the probe tip 112. In one exemplary embodiment, at a location upstream from the branch connection 122, a restriction orifice 140 may be disposed in the central parameter sensing tubular portion 120.

As the plunger 126 moves along the length L3 towards distal end 124" of the proximal tubular syringe portion 124, the pressure inside the central pressure sensing tubular portion 120 is measured (downstream of restriction orifice 140 when the restriction orifice 140 is present) using pressure meter P that is in fluid communication with the central pressure sensing tubular portion 120 and the distal tubular probe portion 110 via the branch connection 122.

When the plunger 126 moves the pressure at pressure meter P versus time characterizes the interaction of the gas meniscus at the tip 112 of the probe 110 with the surface (see FIG. 1, surface 13, and FIGS. 2 and 3, surfaces 31 and 33). The presence of the restriction orifice 140 improves the response time of the pressure meter P since only the volume of the stream probe 100 downstream of the restriction orifice 140 is relevant and the stream probe 100 behaves more closely or approximately as a flow source rather than a pressure source. The volume upstream of the restriction orifice 140 becomes less relevant.

For the bubble method, the pressure difference is generally constant, which means that the bubble size varies and so the bubble rate varies with constant plunger velocity, because the volume in the system changes. A reciprocally moveable plunger may be used to obtain a fixed bubble rate. As described above, in one exemplary embodiment, the pressure sensor P may function either alternatively or additionally as a flow sensor, e.g., as a differential pressure sensor. Those skilled in the art will recognize that flow of the fluid stream or second fluid 130 through the distal probe tip 112 may be detected by means other than pressure sensors such as pressure sensor P, e.g., acoustically or thermally. The embodiments are not limited in this context. Consequently, the movement of the plunger 126 induces a change in pressure or volumetric or mass flow through the distal probe tip 112.

Figure 5:
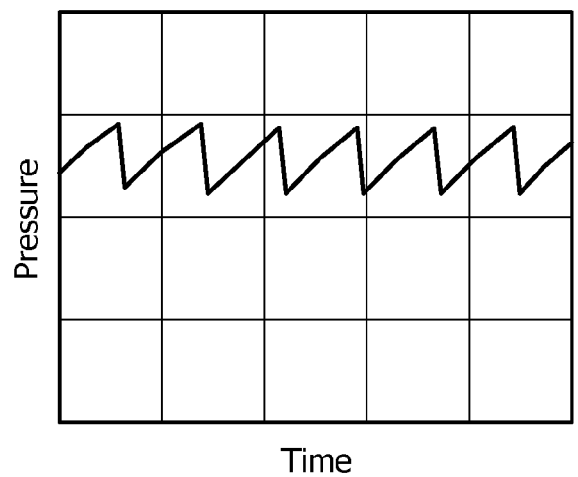
FIG. 5 illustrates a sample pressure measurement of the stream probe of FIG. 4A as a function of time.

FIG. 5 illustrates an example of a pressure signal (measured in Newtons/sq. meter, $N/m^2$) as a function of time (1 division corresponds with a second) utilizing the stream probe 100 of FIG. 4A. The regular variation of the signal is caused by the regular release of gas bubbles at the probe tip 112.

The sensitivity of the pressure readings can be increased by carefully choosing the dimensions of the components. The total volume V1 (equal to A1×L1) plus volume V2 (equal to A2×L2) plus volume V3 (equal to A3×L3) from both the tube 120 and the syringe 124 together with the probe 110, form an acoustical low-pass filter. In the exemplary stream probe 100 of FIG. 4A, the cross-sectional area A3 is greater than the cross-sectional area A2 which in turn is greater than the cross-sectional area A1. The gas flow resistance in the system should be designed small enough to have a good system response time. When bubble-induced pressure differences are recorded, then the ratio between bubble volume and total system volume should be large enough to have a sufficient pressure difference signal due to air bubble release at the probe tip 112. Also the thermo-viscous losses of the pressure wave interacting with the walls of tube 120 as well as the probe 110 must be taken into account, as they can lead to a loss of signal.

In the stream probe 100 illustrated in FIG. 4A, the three volumes differ from one another as an example. However, the three volumes could be equal to one another or the pump volume could be less than the probe volume.

FIG. 4B illustrates an alternate exemplary embodiment of a stream probe according to the present disclosure. More particularly, in stream probe 100', the central parameter sensing portion 120 of stream probe 100 in FIG. 4A is omitted and stream probe 100' includes only proximal pump portion 124 and distal probe portion 110. A pressure sensor P1 is now exemplarily positioned at plunger 126' to sense pressure in the proximal pump portion 124 via an aperture 128 in the plunger 126'.

Alternatively, a pressure sensor P2 may be positioned in the distal probe portion 110 at a mechanical connection 230. In a similar manner as described above with respect to FIG. 4A and restriction orifice 140, in one exemplary embodiment, a restriction orifice 240 may be disposed in the distal probe portion 110 upstream of the mechanical connection 230 and thus upstream of pressure sensor P2. Again, the presence of the restriction orifice 240 improves the response time of the pressure meter P2 since only the volume of the stream probe 100' downstream of the restriction orifice 240 is relevant and the stream probe 100' behaves more closely or approximately as a flow source rather than a pressure source. The volume upstream of the restriction orifice 240 becomes less relevant.

However, it should be noted that for the case of pressure sensor P1, the restriction orifice 240 is optional and is not required for proper sensing of the pressure in distal probe portion 110.

In one exemplary embodiment, the pressure sensor P2 may function either alternatively or additionally as a flow sensor, e.g., as a differential pressure sensor. Those skilled in the art will recognize that flow of the second fluid through the distal probe tip 112 may be detected by means other than pressure sensors such as pressure sensor P2, e.g., acoustically or thermally. The embodiments are not limited in this context. Consequently, the movement of the plunger 126 induces a change in pressure or volumetric or mass flow through the distal probe tip 112.

In a similar manner as described with respect to stream probe 100 in FIG. 4A, volume V3 of the proximal pump portion 124 may be greater than volume V1 of the distal probe portion 110 in stream probe 100' in FIG. 4B, as illustrated. Alternatively, the two volumes may be equal to one another or volume V3 may be less than volume V1.

It should be noted that when restriction orifice 140 is present in stream probe 100 illustrated in FIG. 4A, the volume V3 and the portion of the volume V2 upstream of the restriction orifice 140 become less relevant to the pressure response as compared to the volume in the portion of volume V2 downstream of the restriction orifice 140 and the volume V1.

Similarly, when restriction orifice 240 is present in stream probe 100' illustrated in FIG. 4B, the volume V3 and the volume V1 upstream of restriction orifice 240 become less relevant to the pressure response as compared to the volume V1 downstream of the restriction orifice 240.

Additionally, those skilled in the art will recognize that the restriction of flow via orifices 140 and 240 may be effected by crimping central parameter sensing tubular portion 120 or distal probe portion 110 in lieu of installing a restriction orifice. As defined herein, a restriction orifice includes a crimped section of tubing.

Alternatively, a parameter sensor represented by strain gauge 132 may be disposed on the external surface of the distal probe 110. The strain gauge 132 may also be disposed on the external surface of the proximal pump portion 124 (not shown). The strain readings sensed by strain gauge 132 may be read directly or converted to pressure readings as a function of time to yield a readout similar to FIG. 5 as an alternative method to determine the release of gas bubbles at the probe tip 112.

FIG. 4C illustrates another exemplary embodiment of the stream probe more particularly of FIG. 4A and of FIG. 4B having another exemplary embodiment of a pump portion supplying a generally continuous stream of gas via a tube to a probe tip while sensing a parameter indicative of blockage of flow in the stream probe, which may, in turn, be indicative of plaque or other substance blocking flow in the stream probe. More particularly, stream probe 100" exemplifies a fluid pump designed to provide a generally continuous flow, which is generally advantageous in operation. Stream probe 100" is generally similar to stream probe 100 of FIG. 4A and includes distal probe portion 110 and distal probe tip 112 and central parameter sensing portion 120' which also includes parameter sensor P represented by a pressure sensor and also may include restriction orifice 140 upstream of the pressure sensor P.

Stream probe 100" differs from stream probe 100 in that proximal pump portion 124 is replaced by proximal pump portion 142 wherein, in place of reciprocating plunger 126, that reciprocates along center line axis X1-X1' of the proximal pump portion 124, diaphragm pump 150 reciprocates in a direction transverse to longitudinal axis X2-X2' of proximal pump portion 124, the direction of reciprocation of diaphragm pump 150 indicated by double arrow Y1-Y2, The diaphragm pump 150 includes a motor 152 (represented by a shaft) and an eccentric mechanism 154 which is operatively connected to a connecting rod or shaft 156 that in turn is operatively connected to a flexible or compressible diaphragm 158

An air intake supply path 160 is in fluid communication with proximal pump portion 142 to supply air from the ambient surroundings to the proximal pump portion 142. The air intake supply path 160 includes an intake conduit member 162 having a suction intake port 162a from the ambient air and a downstream connection 162b to the proximal pump portion 142, thereby providing fluid communication between the proximal pump portion 142 and the ambient air via the suction port 162a. A suction flow interruption device 164, e.g. a check valve, is disposed in the intake conduit member 162 between the suction port 162a and the downstream connection 162b. A suction intake filter 166, e.g. a membrane made from a porous material such as expanded polytetraflouroethylene ePTFE (sold under the trade name Gore-Tex® by W. L. Gore & Associates, Inc., Elkton, Md., USA) may be disposed in the air intake supply path 160 in the intake conduit member 162 upstream of the suction flow interruption device 164 and generally in proximity of the suction intake port 162a to facilitate periodic replacement.

The central parameter sensing portion 120' serves also as a discharge flow path for the proximal pump portion 142. A proximal pump portion discharge flow path flow interruption device 168, e.g., a check valve, is disposed in the central parameter sensing portion 120' upstream of the parameter sensor P and, when present, the restriction orifice 140.

Thus the distal tip 112 is in fluid communication with the suction intake port 162a of the air intake conduit member 162 of the air intake supply path 160 via the distal probe portion 110, the central parameter sensing portion 120' and the proximal pump portion 142.

During operation of the motor 152, the motor 152 rotates, in the direction indicated by arrow Z, the eccentric mechanism 154, thereby imparting a reciprocating motion to the connecting rod or shaft 156. When the connecting rod or shaft 156 moves in the direction of arrow Y1 towards the motor 152, the flexible or compressible diaphragm 158 moves also in the direction of arrow Y1 towards the motor 152, thereby causing a reduction in pressure within the interior volume V' of the proximal pump portion 142. The reduction in pressure causes pump portion discharge flow path flow interruption device 168 to close and causes the suction flow interruption device 164 to open, thereby drawing air through the suction intake port 162a.

The eccentric mechanism 154 continues to rotate in the direction of arrow Z, until the connecting rod or shaft 156 moves in the direction of arrow Y2 away from the motor 152 and towards the flexible or compressible diaphragm 158 such that the flexible or compressible diaphragm 158 moves also in the direction of arrow Y2 towards the interior volume V', thereby causing an increase in pressure within the interior volume V' of the proximal pump portion 142. The increase in pressure causes the suction flow interruption device 164 to close and the pump portion discharge flow path flow interruption device 168 to open, thereby causing air flow through the central parameter sensing portion 120' and the distal probe portion 110 through the distal tip 112.

When restriction orifice 140 is deployed and disposed in the central parameter sensing portion 120', which, as indicated above, serves also as a discharge flow path for the proximal pump portion 142, a low pass filter function is performed by volume V''' between pump portion discharge flow path flow interruption device 168 and restriction orifice 140. Thus, when restriction orifice 140 is deployed, pump portion discharge flow path flow interruption device 168 must be upstream of the restriction orifice 140. As a result, high frequency pulsations are filtered out of the air flow to the distal tip 112.

Figure 6:
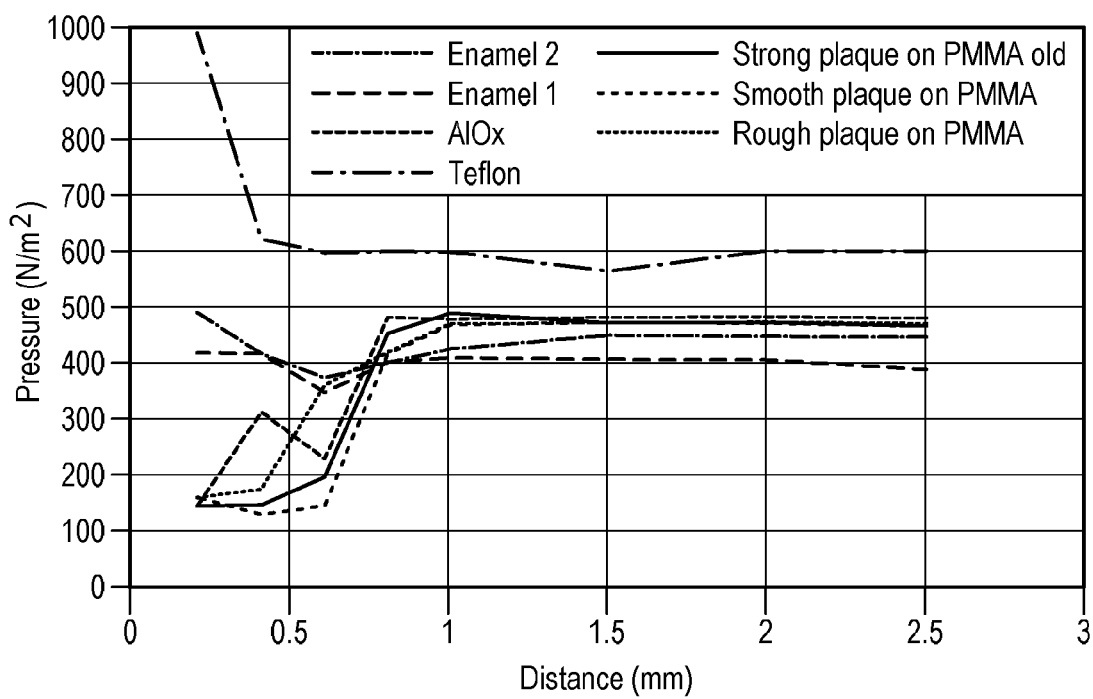
FIG. 6 illustrates a sample pressure signal amplitude as a function of distance of the probe tip of FIG. 4A to various dental surfaces.

FIG. 6 shows pressure amplitude data as a function of the distance d1 or d2 between probe tip 112 and surface 13 in FIG. 1 or surfaces 31 and 33 in FIG. 2, measured for different surfaces. A plastic needle with 0.42 mm inner diameter was used. Clear differences are visible at distances up to 0.6 mm, where the most hydrophobic surface (Teflon) gives the largest pressure signal, while the most hydrophilic surface (plaque) gives the lowest signal.

It should be noted that the data presented in FIGS. 5 and 6 were taken without the inclusion of restriction orifices.

FIGS. 1-6 have described a first method of detecting the presence of a substance on a surface, which includes the measurement of bubble release from a tip (by pressure and/or pressure variations and/or bubble size and/or bubble release rate) as a method of detecting, for example, dental plaque at the probe tip 112. As described above with respect to FIGS. 1 and 2 and 6, the probe tip 112 is positioned at a distance d1 or d2 away from the surface such as surface 13 in FIG. 1 or surfaces 31 and 33 in FIG. 2.

It should be noted that although the method of bubble generation and detection has been described with respect to the second fluid being a gas such as air, the method may also be effective when the second fluid is a liquid, wherein water droplets instead of gas bubbles are created.

Additionally, the method may be affected with constant pressure and measurement of the variable fluid outflow. The apparatus may record the variable pressure and/or the variable flow of the second fluid. In one exemplary embodiment, the pressure is recorded and the flow of the second fluid is controlled, e.g., the flow is kept constant. In another exemplary embodiment, the flow is recorded and the pressure of the second fluid is controlled, e.g., the pressure is kept constant.

Figure 7:
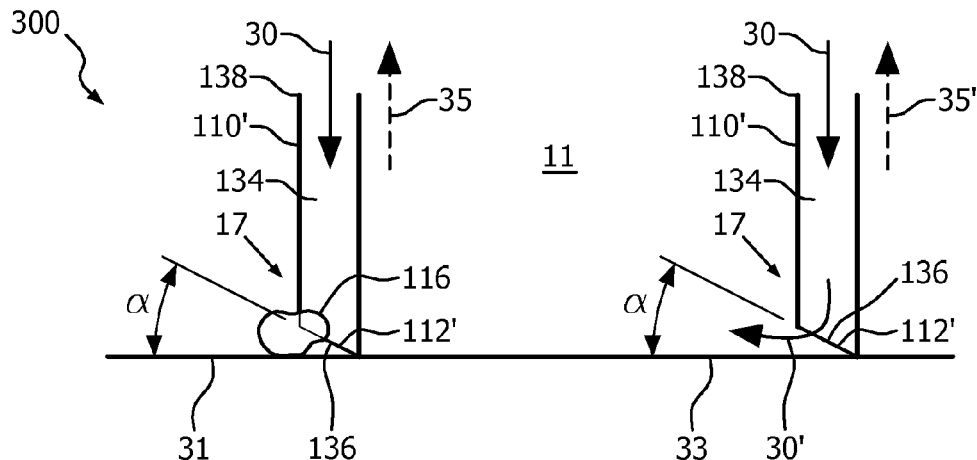
FIG. 7 illustrates a system for detecting the presence of a substance on a surface according to one exemplary embodiment of the present disclosure wherein on the left is illustrated one embodiment of a stream probe having a partial blockage from dental surface material such as dental plaque while on the right is illustrated one embodiment of an unblocked stream probe.

In a second method of detecting the presence of a substance on a surface according to the exemplary embodiments of the present disclosure, FIG. 7 illustrates the influence of blocking of the probe tip 112 of the probe 110 of FIG. 4A, 4B or 4C. The probe or stream probe tubular member or stream probe 110' illustrated in FIG. 7 includes a proximal end 138 and interior channel 134. The stream probe or stream probe tubular member 110' differs from stream probe 110 in FIG. 4A, 4B or 4C and 6 in that the stream probe 110' includes a chamfered or beveled distal tip 112' having an open port 136 that is chamfered at an angle α with respect to the horizontal surface 31 or 33 such that passage of the second fluid medium through the distal tip 112, now designated as second fluid medium 30' since it has exited from the distal tip 112', is also enabled when the distal tip 112' touches the surface 31 or 33, and the second fluid medium 30' is also enabled to flow through the chamfered open port 136. The angle α of the chamfer of the open port 136 is such that passage of the second fluid medium 30' through the distal tip 112' is at least partially obstructed when the distal tip 112' touches the surface 31 or 33 and a substance 116, such as viscoelastic material 116, at least partially obstructs the passage of fluid through the open port 136 of the distal tip 112'. Although only one probe 110' is required to detect obstruction of the passage of fluid, in one exemplary embodiment, it may be desired to deploy at least two probes 110' as a system 3000 to detect obstruction of the passage of fluid (see the discussion below for FIGS. 13-17 and FIGS. 19-21).

Other shapes for the distal tips of the distal probe portions of the various embodiments are contemplated herein for preventing blockage or obstruction of the passage of fluid through the open ports of the distal tips. These shapes also prevent false positives by ensuring that on a flat surface a flow escapes from the distal tips. The various shapes of the distal tips and advantages thereof are described below with reference to FIGS. 23-29.

Alternatively, the probe tips 112 of FIG. 1, 2, 4A or 4B are utilized without chamfered or beveled ends and simply held at an angle (such as angle α) to the surface 31 or 33. In one exemplary embodiment, the substance has a nonzero contact angle with water. In one exemplary embodiment, the substance with a nonzero contact angle with water is enamel.

As illustrated on the left portion of FIG. 7, when the probe tip 112' becomes blocked by viscoelastic material 116 from the dental surface 31, then the fluid such as gas 30 will flow less easily out of the tip 112', as compared to when probe tip 112' is not blocked (second fluid medium 30') and is without dental material at the tip 112' or at dental surface 33, as illustrated in the right portion of FIG. 7.

Figure 8:
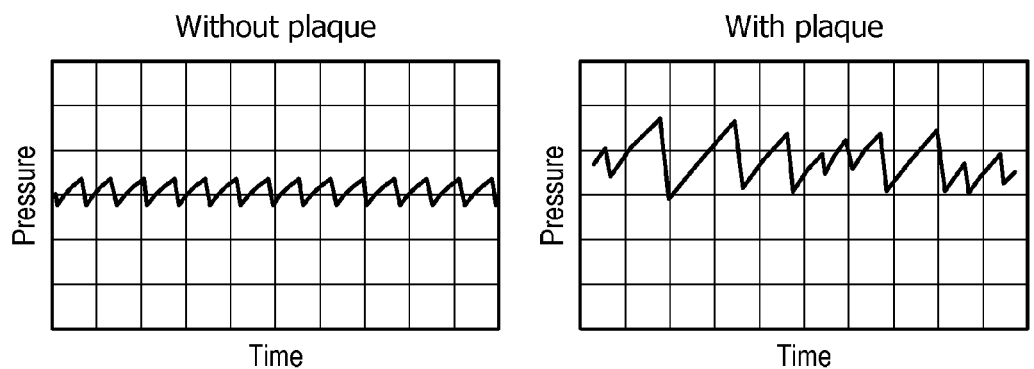
FIG. 8 illustrates on the left a sample pressure measurement versus time for the unblocked stream probe of FIG. 7 and on the right illustrates a sample pressure measurement versus time for the partially blocked stream probe of FIG. 7.

FIG. 8 illustrates pressure signals of a probe tip, e.g., a metal needle with a bevel, moving on enamel without plaque, as illustrated on the left, and on a sample with a plaque layer, as illustrated on the right. The increase in pressure seen in the right portion, attributed to obstruction of the needle opening by the plaque, can be sensed to detect if plaque is present.

Figure 9:
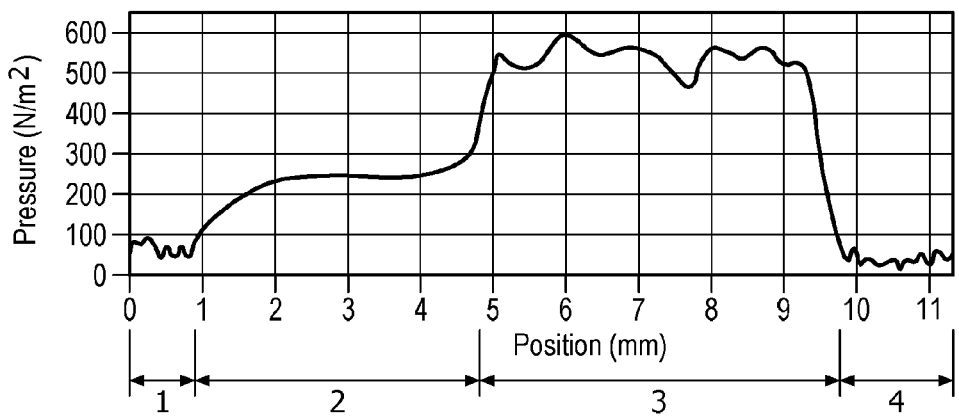
FIG. 9 illustrates a pressure signal versus time for a stream probe having a Teflon tip in accordance with one exemplary embodiment of the present disclosure.

FIG. 9 illustrates pressure signals of an airflow from a Teflon tip moving over water, region 1, PMMA (polymethyl methylacrylate) region 2, PMMA with plaque region 3, and water region 4. The tip moves (from left to right) over water region 1, PMMA region 2, PMMA with plaque region 3, and again over water region 4. The Teflon tip is not shown).

When reference is made to pressure differences herein, consideration of the following should be taken into account. In FIG. 8, the fluid stream 30 is obstructed when the pressure increases on the left panel. So the parameter of interest is the average pressure or average or momentary peak pressure.

In contrast, FIG. 9 illustrates identical signals for a smaller probe tip, in which case a much smoother signal is obtained.

The data presented in FIGS. 8 and 9 were taken without the inclusion of restriction orifices.

In preliminary experiments according to FIG. 2, we have observed the following:

Dental plaque (in wet state) is more hydrophilic than clean enamel, as shown in FIG. 3.

The release of air bubbles from the tip is measurable by pressure variations. A syringe with constant displacement velocity gives a sawtooth-like signal of pressure as a function of time. This is shown in the oscilloscope photograph in FIG. 5.

In case of close approach between tip and surface, the amplitude of the sawtooth signal is smaller when the probed surface is more hydrophilic than when the surface is less hydrophilic. So, smaller air bubbles are released on the more hydrophilic surface. This is also demonstrated by the measurements in FIG. 6, where the pressure signal amplitude as a function of distance d1 or d2 from the tip to the surface (see FIGS. 1 and 2) is given for different surfaces.

In preliminary experiments according to FIG. 7, we have observed the following:

An unblocked tip gives a regular release of air bubbles and a sawtooth-like pattern of pressure versus time, when a syringe is used with a constant displacement velocity. See the left panel of FIG. 8.

In an experiment with a metal tip moving through plaque material, an increase of pressure and an irregular sawtooth-like pattern of pressure versus time was observed, due to blocking of the tip by plaque material and opening of the tip by the air. See the right panel of FIG. 8.

In an experiment with a Teflon tip, clear signal differences were seen for different materials at the tip opening (from left to right: tip in water, tip above PMMA, above PMMA with plaque, and again tip in water).

These preliminary experiments indicate that the measurement of bubble release from a tip (by pressure and/or pressure variations and/or bubble size and/or bubble release rate) may become a suitable method to detect dental plaque at the tip. Accordingly, in view of the foregoing, at a minimum, the novel features of the exemplary embodiments of the present disclosure are characterized in that:

(a) fluid medium 14 is brought in contact with surface 13 at probe tip 12, generating interaction zone 17 between tip 12 and surface 13 (see FIG. 1); and (b) the shape and/or dynamics of the medium 14 in the interaction zone 17 depend on the properties of the surface 13 and/or on materials derived from the surface 13; and (c) the pressure and/or shape and/or dynamics of the medium 14 in the interaction zone 17 are detected.

In view of the foregoing description of the two differing methods of detecting the presence of a substance on a surface, the proximal pump portion 124 in FIGS. 4A and 4B effectively functions as a syringe. During injection of the plunger 126 or 126' distally, gas or air flow or liquid flow at the tip 112 in FIGS. 4A and 4B, or tip 112' in FIG. 7, can be pushed outwardly away from the tip (when the plunger is pushed).

During retraction or reverse travel of the plunger 126 or 126', gas or air flow or liquid flow can be suctioned inwardly at the tip 112 or 112' and in towards the probe tube 110 or 110'. In one exemplary embodiment, the plunger 126 or 126' is operated automatically together with the vibration of the bristles of an electric toothbrush or where the bristles are not vibrating (e.g. using the same principle in a dental floss device).

Accordingly, the syringe or pump 124 can be used for the stream method in which flow of gas or air is injected away from the tip 112 and towards the enamel to generate bubbles 32 or 34. The bubbles and locations are detected optically and depending on whether the surface is more hydrophilic such as plaque or less hydrophilic such as enamel, the location of the bubble will determine whether there is plaque present. That is, the surface has a hydrophilicity which differs from the hydrophilicity of the substance to be detected, e.g., enamel has a hydrophilicity which is less than the hydrophilicity of plaque. The tip 112 is located at a particular distance d2 (see FIG. 2) away from the enamel regardless of whether plaque is present or not.

Alternatively, pressure sensing can also be used for the bubble method. Referring also to FIG. 2 and FIG. 4A, the same pump portion 124 functioning as a syringe can be used for the pressure sensing method as follows. Fluid is injected towards the enamel surface 31 or 33. The probe tip 112 is initially located at a particular dimension away from the enamel surface such as d2 in FIG. 2. The pressure signal is monitored as illustrated and described above in FIGS. 5 and 6. Bubble release measurements are performed by pressure and/or pressure variations as described above.

In the second method of detecting the presence of a substance on a surface according to the exemplary embodiments of the present disclosure, as illustrated in FIG. 7, the passage of the second fluid such as gas 30 through the distal tip 112 enables detection of substance 116 that may be present on the surface 31 based on measurement of a signal, correlating to a substance at least partially obstructing the passage of fluid through the open port of the distal tip 112'. The signal may include an increase or decrease in pressure or change in other variables as described above.

Since in one exemplary embodiment at least two probes 110' are utilized, FIG. 7 illustrates a system 300 for detecting the presence of a substance on a surface. In one exemplary embodiment, the probes 110' are in contact with the surface 31 or 33 as described above. If there is no plaque at the surface 33, i.e., flow is unblocked, then the pressure signal is as shown in FIG. 8, left panel. If there is plaque at the surface, e.g., viscoelastic material 116, then the pressure signal is as shown in FIG. 8, right panel.

For practical applications, it is contemplated that the probe or probes 110' have a very small diameter, e.g., less than 0.5 millimeters, such that by their spring function, the probe tips 112' will make contact with the tooth surface 33. So when reaching the plaque the tube is pressed into this layer of plaque. The pressure signals illustrated in FIG. 8 were obtained with a single probe in contact.

Referring again to FIG. 7, in an alternate exemplary embodiment of the second method of detecting the presence of a substance on a surface, fluid is suctioned away from the enamel surface by reverse travel of the plunger 126 or 126' proximally towards the proximal end 124' of the proximal pump portion 124' in FIGS. 4A and 4B. Fluid or gas inflow 30 now becomes fluid or gas outflow 35 as illustrated by the dotted arrows (shown outside of the interior channel 134 for simplicity). If there is plaque 116 present, the plaque either is large enough to block the aperture at the probe tip or is small enough to be suctioned inside the probe channel. The pressure signal becomes an inverted version of FIG. 8. Lower pressure will be obtained in the presence of plaque.

As defined herein, regardless of the direction of flow of the second fluid through the probe tip, obstruction can mean either a direct obstruction by a substance at least partially, including entirely, blocking the tip itself or obstruction can mean indirectly by the presence of a substance in the vicinity of the probe tip opening thereby perturbing the flow field of the second fluid.

In addition to performing the first and second methods by maintaining a constant velocity of the plunger, the methods may be performed by maintaining constant pressure in the proximal pump portion and measuring the variable outflow of the second fluid from the probe tip. The readout and control can be configured in different ways. For example, the apparatus may record the variable pressure and/or the variable flow of the second fluid. In one exemplary embodiment, the pressure is recorded and the flow of the second fluid is controlled, e.g., the flow is kept constant. In another exemplary embodiment, the flow is recorded and the pressure of the second fluid is controlled, e.g., the pressure is kept constant.

Additionally, when two or more probes 110' are deployed for system 300, one of the probes 110' may include pressure sensing of the flow of the second fluid through the distal probe tip 112' while another of the probes 110' may include strain sensing or flow sensing.

Additionally, for either the first method of bubble detection or the second method of obstruction, although the flow of the second fluid is generally laminar, turbulent flow of the second fluid is also within the scope of present disclosure.

Figure 10:
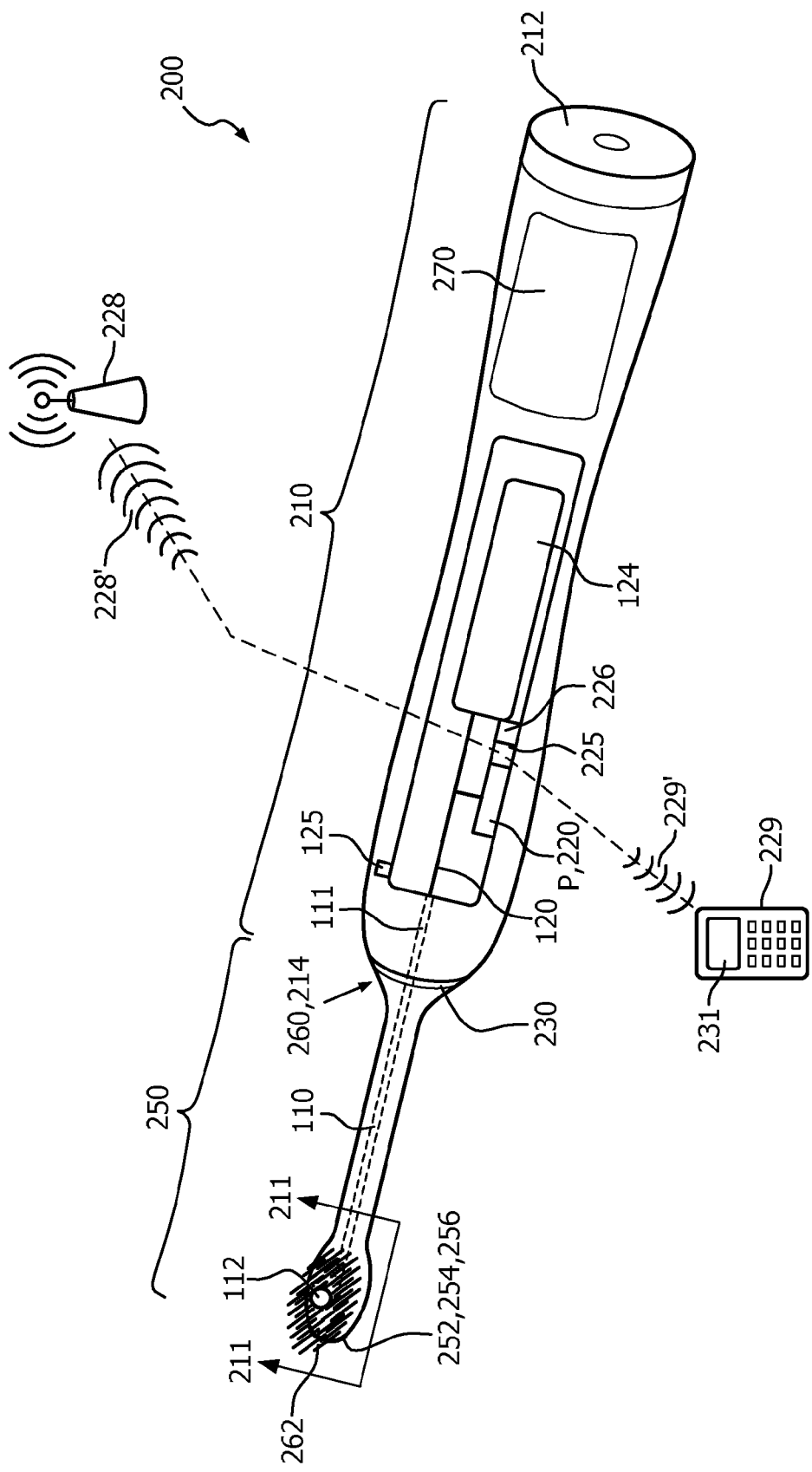
FIG. 10 illustrates a stream probe system incorporated into a dental apparatus such as an electric toothbrush in accordance with one exemplary embodiment of the present disclosure.

FIG. 10 illustrates a detection apparatus or instrument for detecting the presence of a substance on a surface according to one exemplary embodiment of the present disclosure wherein the detection apparatus is exemplified by the integration of the stream probe into a dental apparatus such as a tooth brush, forming thereby a detection apparatus for detecting the presence of a substance on a surface.

Traditionally an electric toothbrush system, such as the Philips Sonicare toothbrush mentioned above, comprises a body component and a brush component. Generally, the electronic components (motor, user interface UI, display, battery etc.) are housed in the body, whilst the brush component does not comprise electronic components. For this reason, the brush component is easily exchangeable and replaceable at a reasonable cost.

In one exemplary embodiment, detection apparatus or instrument 200, e.g., a dental cleaning instrument such as an electric toothbrush, is configured with a proximal body portion 210 and a distal oral insertion portion 250. The proximal body portion 210 defines a proximal end 212 and a distal end 214. The distal oral insertion portion 250 defines a proximal end 260 and a distal end 262. The distal end 262 includes a vibrating brush 252 with brush base 256 and bristles 254 and a distal portion of an air stream probe or a liquid stream probe such as air stream probe 100 described above with respect to FIG. 4A or 100' with respect to FIG. 4B. In conjunction with FIG. 4A, 4B or 4C, the detection apparatus 200 is configured such that active components, e.g., mechanical, electrical or electronic components are incorporated within, or disposed externally on, the proximal body portion 210, whilst the passive components such as distal probe portion 110, are incorporated within, or disposed externally on, a distal portion, exemplified by, but not limited to, distal oral insertion portion 250. More particularly, probe tip 112 of probe 110 is incorporated close to or within the bristles 254 so as to intermingle with the bristles 254, while the central parameter sensing tubular portion 120 and the proximal tubular syringe portion 124 are incorporated within, or disposed externally on, proximal body portion 210. Thus, the distal probe portion 110 is at least partially in contact with the distal oral insertion portion 250. A portion 111 of the distal probe tip 110 is disposed on the proximal body portion 210 and thus is a proximal probe portion.

In one exemplary embodiment, the distal oral insertion portion 250, including the brush 252 that includes brush base 256 and bristles 254, is exchangeable or replaceable. That is, the proximal body portion 210 is removably attachable to the distal oral insertion portion 250.

Contact to the proximal body portion 210 with the active parts by the distal oral insertion portion 250 is provided by a mechanical connection 230 on the proximal body portion 210 that is disposed to interface the distal end 214 of proximal body portion 210 and proximal end 260 of distal oral insertion portion 250, thereby interfacing the portion 111 of the distal probe tip 110 with distal probe tip 110 disposed on the distal oral insertion portion 250 such that an air stream is generated and the pressure is sensed, such as at the location of parameter sensor P2 in FIG. 4B or parameter sensors P in FIG. 4A or 4C. Based on the pressure sensor signal, it is concluded if plaque is present at the area of the probe tip 112. Thus, the proximal body portion 210 is removably attachable to the distal probe portion, illustrated in FIG. 10 as the distal oral insertion portion 250 via the mechanical connection 230. Those skilled in the art will recognize that, although the detection apparatus or instrument 200 is illustrated in FIG. 10 such that the distal oral insertion portion 250 and the proximal body portion 210 are removably attachable from one another, and thus either one is replaceable, the detection apparatus or instrument 200 can be configured or formed as a unitary, integrated combined apparatus or instrument wherein the distal oral insertion portion 250 and the proximal body portion 210 are not readily detachable from one another.

In addition, the stream probes 100, 100' or 100" may be utilized independently without including the brush 252, the brush base 256, or the bristles 254. such as illustrated in FIGS. 4A, 4B and 4C. The detection apparatus or instrument 200 may be applied either with or without the brush 252, the brush base 256, or the bristles 254 both to dental and non-dental applications to detect the presence of a substance on a surface.

When the detection apparatus or instrument 200 is designed as a dental cleaning instrument, the probe 110 may be dimensioned and made from materials selected so as to yield a rotational stiffness that is generally equivalent to the rotational stiffness of the bristles 254 such that the probe 110 sweeps an area during operation generally equivalent to the sweep area and timing of the bristle operation so as to reduce any potential discomfort to the user. The variables contributing to the design of the stiffness include the dimensions, the mass and the modulus of elasticity of the material selected.

In one exemplary embodiment, the active components comprise the pressure sensor P as described above. In conjunction with FIG. 1, the sensor P is used to sense the shape and/or dynamics of the medium 14 in the interaction zone 17. Such a sensor has the advantage that it is robust and simple to use. The sensor P is in electrical communication with detection electronics 220 that include a controller 225 that is in electrical communication therewith.

In an alternate exemplary embodiment, the active component may comprise an optical, electrical or acoustic sensor such as, for example, a microphone, in order to sense the shape and/or dynamics of the medium 14 in the interaction zone 17.

The controller 225 can be a processor, microcontroller, a system on chip (SOC), field programmable gate array (FPGA), etc. Collectively the one or more components, which can include a processor, microcontroller, SOC, and/or FPGA, for performing the various functions and operations described herein are part of a controller, as recited, for example, in the claims. The controller 225 can be provided as a single integrated circuit (IC) chip which can be mounted on a single printed circuit board (PCB). Alternatively, the various circuit components of the controller, including, for example, the processor, microcontroller, etc. are provided as one or more integrated circuit chips. That is, the various circuit components are located on one or more integrated circuit chips.

Furthermore, the active components enable a method of generating an air or liquid stream. A combined air with liquid stream is possible as well. The method may comprise an electrical or a mechanical pumping method, whereby the mechanical method may comprise a spring component which is mechanically activated, e.g., wherein plunger 126 in FIG. 4 is mechanically activated. In one exemplary embodiment, the method of generating the air stream is an electrical pumping principle, as this combines well with the pressure sensing component described above. In other exemplary embodiments, air may be replaced by other gases, e.g., nitrogen or carbon dioxide. In such exemplary embodiments, while the proximal body portion 210 may include the proximal pump portion 124 and the plunger 126 or other types of pumps to generate either constant pressure or constant flow of fluid, the proximal body portion 210 may include a container of compressed gas (not shown) that is sized to fit within the proximal body portion 210 and is capable of providing either constant pressure or constant flow via a valve control system (not shown).

In yet another exemplary embodiment, the passive components comprise only a tube with an opening at the end, such as probe 110 and distal tip 112 (see FIG. 10).

In still another exemplary embodiment, connection of the active and passive components is realized by a mechanical coupling 230 of the tube to the output of the pressure sensor. Such a coupling is ideally substantially pressure sealed. Pressure values are relatively low (<<1 bar).

In operation, the sensing is carried out in a repetitive manner during the tooth brushing process. In a preferred exemplary embodiment, sensing is carried out at a frequency>1 Hz, more preferably >5 Hz and even more preferably >10 Hz. Such a high frequency embodiment facilitates the dynamic and real time measurement of plaque removal as the toothbrush is moved from tooth to tooth, as several measurements may be made on an individual tooth (the dwell time on a given tooth is typically of the order of 1-2 seconds).

In conjunction with FIG. 1, as described above, the shape and/or dynamics of the medium 14 in the interaction zone 17 depend on the properties of the surface 13 and/or on materials derived from the surface 13, the pressure and/or shape and/or dynamics of the medium 14 in the interaction zone 17 are detected and a determination is made by the controller 225 as to whether a level of plaque exceeding a predetermined maximum permissible level of plaque is detected at the particular dental surface 13.

If a positive detection is made, no progression or advancement signal is transmitted to the user of the electric toothbrush until a predetermined maximum permissible plaque level is achieved at the particular dental surface 13 by continued cleaning at the dental surface 13 of that particular tooth.

Upon reduction of the level of plaque to at or below the maximum permissible plaque level, i.e., a negative detection is made, a progression signal or advancement signal is transmitted to the user to inform the user that it is acceptable to progress to an adjacent tooth or other teeth by moving the vibrating brush and probe tip of the dental apparatus.

Alternatively, if a positive detection is made, a signal is transmitted to the user of the electric toothbrush having an integrated stream probe plaque detection system to continue brushing the particular tooth.

Furthermore, there are several preferred modes of operation of the passive component in the brush.

In a first mode operation, the tube is configured such that the tip of the tube is acoustically uncoupled from the vibration of the brush (which vibrates at about 265 Hz in a Philips Sonicare toothbrush). This may be achieved by only weakly coupling the tube to the brush head.

In a further mode of operation, the tube is configured such that the tip of the tube is static. This may be achieved by choosing the mechanical properties of the tube (stiffness, mass, length) such that the tip of the probe is at a static node of vibration at the driving frequency. Such a situation may be helped by adding additional weight to the end of the tube close to the opening.

Figure 11:
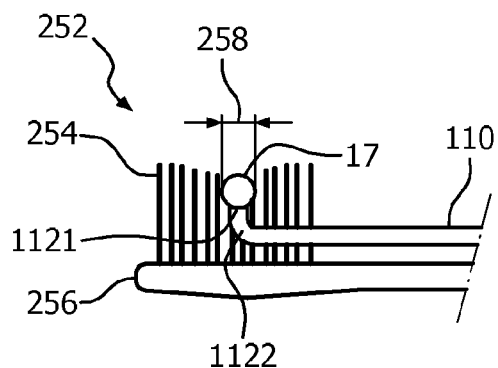
FIG. 11 illustrates a view of the brush of the dental apparatus taken along line 211-211 of FIG. 10 having a stream probe tip at a position within the bristles of the brush.

As illustrated in FIG. 11, which is a partial cross-sectional view of distal oral insertion portion 250 in FIG. 10, in a further exemplary embodiment, the effect of the motion of bristles of the toothbrush on the sensing function is reduced by incorporating a spacing 258 around the tube where the bristles are removed. More particularly, probe 110 in FIG. 11 illustrates a brush head 252 that includes base 256 and bristles 254 that protrude generally orthogonally from the base 256. Spacing 258 is positioned with removed bristle wires around probe tip 1121. The probe tip 1121 differs from probe tips 112 and 112' in that probe tip 1121 includes a 90 degree elbow 1122 so as to enable fluid flow through the probe 110 towards the surface 31 or 33.

In one exemplary embodiment, the spacing 258 should be of the order of the amplitude of the vibration of the bristles 254. In practice, the bristles vibrate with an amplitude of around 1-2 mm. This makes the sensing more robust.

Figure 12:
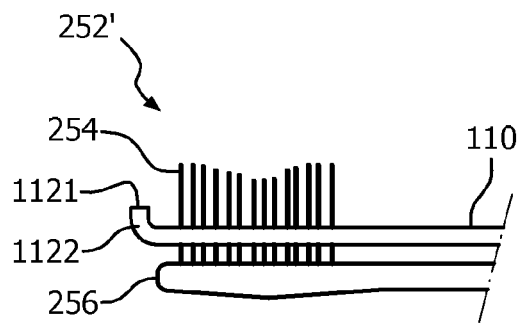
FIG. 12 illustrates an alternate exemplary embodiment of the view of the brush of FIG. 11 wherein the stream probe tip extends distally from the bristles of the brush.
Figure 13:
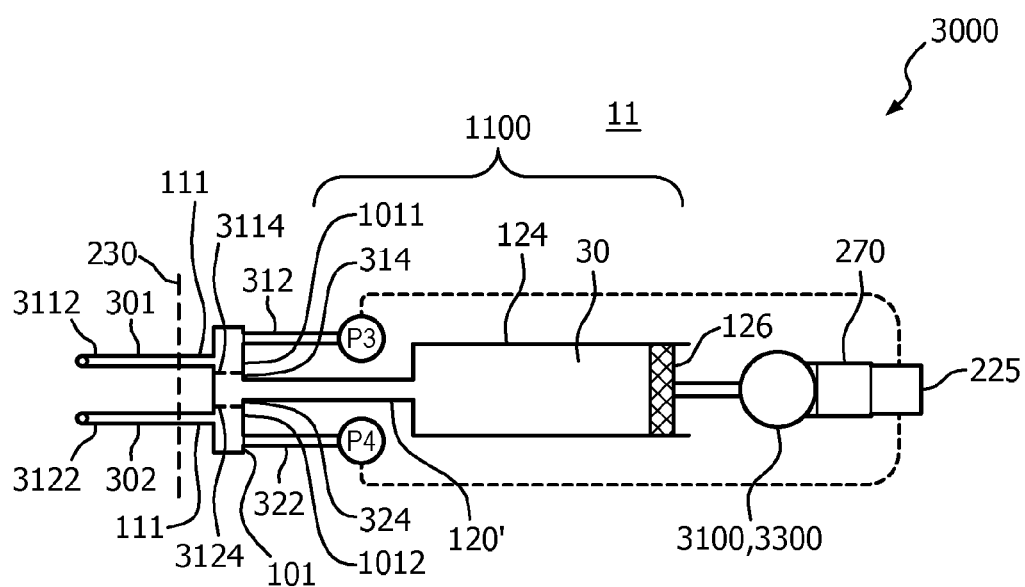
FIG. 13 illustrates an alternate exemplary embodiment of the stream probe of FIG. 4A having a pump portion supplying a continuous stream of gas via a tube to two probe tips while measuring the internal tube pressure at the inlet to a first stream probe tip and the internal pressure at the inlet to a second stream probe tip.

In a further exemplary embodiment, as illustrated in FIG. 12, the probe tip 1121 is situated distally beyond the area covered by the bristles 254. This makes it possible to detect plaque which is present beyond the present position of the brush, for example plaque which has been missed by an incomplete brushing action.

As a further detail, ideally the angle of the brush 252 while brushing is 45 degrees with respect to the tooth surface 31 or 33. Ideally the angle of the probe tip 1121 is close to 0 degrees with respect to the tooth surface 31 or 33. At least two probes 110 and correspondingly at least two pressure sensors and two pumps with a tip end 1121 of 45 degrees with respect to the tooth surface 31 or 33, so that always one probe is interfacing optimally the surface 31 or 33.

In still a further exemplary embodiment, a plurality of probes are incorporated in the brush. These probes may alternatively be disposed or utilized at least as follows:

(a) positioned at multiple positions around the brush, to sense for (missed) plaque more effectively, or (b) used for differential measurements to determine the degree and effectiveness of the plaque removal.

In one exemplary embodiment, the plurality of probes may be realized with a single active sensing component and a multiplicity of passive components, such as tubes, attached to a single pressure sensor. Alternatively, a plurality of active and passive sensing components may be used.

The end of the tube may have many dimensions, as described above. In alternative exemplary embodiments, the tip of the tube will be spaced from the surface of the tooth using a mechanical spacer. In some exemplary embodiments, the opening may be made at an angle to the tube.

FIGS. 13-22 illustrate examples of a detection system 3000 for detecting the presence of a substance on a surface that employs the foregoing principles for detecting the presence of a substance on a surface via multiple stream probes. More particularly, in one exemplary embodiment of the present disclosure, the system 3000 includes a detection apparatus 1100 for detecting the presence of a substance on a surface such as an air stream probe having proximal pump portion 124 and plunger 126 as described above with respect to FIG. 4A and FIG. 10. It should be noted, however, that in lieu of proximal pump portion 124 and plunger 126, proximal pump portion 142 and diaphragm pump 150, as described above with respect to FIG. 4C, may also be deployed to provide a generally continuous flow 1100 for detecting the presence of a substance on a surface in a similar manner as described below with respect to the proximal pump portion 124 and plunger 126.

The proximal pump portion 124 includes a central parameter sensing tubular portion 120' configured with a distal tee connection 101 defining a first leg 1011 and a second leg 1012. First stream probe 301 having a distal probe tip 3112 is fluidically coupled to the first leg 1011 and second stream probe 302 having a distal probe tip 3122 is fluidically coupled to the second leg 1012.

A pressure sensor P3 is connected to the first leg 1011 via branch connection 312 in the vicinity of the first stream probe 301 and a pressure sensor P4 is connected via branch connection 322 in the vicinity of second stream probe 302 to the second leg 1012. In as similar manner as with respect to stream probe 100 described above with respect to FIG. 4A, stream probe 100' described above with respect to FIG. 4B and stream probe 100" described above with respect to FIG. 4C, the stream probe 1100 may include a restriction orifice 3114 disposed in first leg 1011 downstream of junction 314 between central parameter sensing tubular portion 120' and the first leg 1011 and upstream of first stream probe 301 and pressure sensor P3. Similarly, a restriction orifice 3124 may be disposed in second leg 1012 downstream of junction 324 between central parameter sensing tubular portion 120' and the second leg 1012 and upstream of second stream probe 302 and pressure sensor P4. Again, the presence of the restriction orifices 3114 and 3124 improves the response time of the pressure meters P3 and P4 since only the volume of the stream probe 1100 downstream of the restriction orifices 3114 and 3124 is relevant. The air flow into each pressure sensor P3 and P4 becomes approximately independent since the pressure drops occur predominantly across the restriction orifices 3114 and 3124 and the stream probe 1100 behaves more closely or approximately as a flow source rather than a pressure source. The volume upstream of the restriction orifice 240 becomes less relevant. The pressure sensors P3 and P4 can each generally sense a pressure rise separately while being driven by single plunger 126.

Additionally, those skilled in the art will recognize that the restriction of flow via orifices 3114 and 3124 may be effected by crimping the distal tee connection 101 in the vicinity of the junctions 314 and 324 in lieu of installing a restriction orifice. Again, as defined herein, a restriction orifice includes a crimped section of tubing.

In a similar manner as described above with respect to detection apparatus 200 illustrated in FIG. 10, the sensors P3 and P4 are in electrical communication with detection electronics and a controller such as detection electronics 220 that include controller 225 that is in electrical communication therewith (see FIG. 10).

Upon detection of plaque by the detection electronics 220, the controller 225 generates a signal or an action step. Referring to FIG. 10, in one exemplary embodiment, the controller 225 is in electrical communication with an audible or visible alarm 226 located on the such as an intermittent sound such as a buzzer and/or a constant or intermittent light that is intended to communicate to the user to continue brushing his or her teeth or the subject's teeth at that particular location.

In one exemplary embodiment, based upon the signals detected by the detector electronics 220, the controller 225 may record data to generate an estimate of the quantity of plaque that is present on the teeth. The data may be in the form of a numerical quantity appearing on a screen 125 in electrical communication with the detector electronics 220 and the controller 225. The screen 125 may be located on, or extending from, the proximal body portion 210 as illustrated in FIG. 10. Those skilled in the art will recognize that the screen 125 may be located at other positions suitable for the user to monitor the data presented on the screen.

The signalling to the user may include the controller 225 configured additionally as a transceiver to transmit and receive a wireless signal 228' to and from a base station 228 with various indicators on the base station that generate the signal to trigger the audible or visual alarm 226 or to record the numerical quantity or other display message such as an animation on the screen 125.

Alternatively, the controller 225 may be configured additionally as a transceiver to transmit and receive a wireless signal 229' to a smart phone 229 that runs application software to generate animations on a screen 231 that signal that plaque has been identified and instruct the user to continue brushing in that location. Alternatively, the application software may present quantitative data on the amount of plaque detected.

FIGS. 14-16 illustrate an alternate distal oral insertion portion 350 that includes a brush 352 with bristles 354 mounted on brush base 356, and as illustrated in FIG. 14 as viewed looking towards the brush base 356 and the upper tips of the bristles 354. As best illustrated in FIGS. 15 and 16, extending generally orthogonally from horizontal upper surface 356' of brush base 356 are distal probe tips 3112 and 3122 which enable multiple fluid flows to be directed towards the surface of interest such as surfaces 31 and 33 in FIGS. 2 and 7. Alternate or additional positions for distal probe tips 3112 and 3122 are illustrated by the dotted lines in the vicinity of the proximal end of the brush base 356 in FIG. 14.

In a similar manner, FIGS. 17-19 illustrate system 3010 for detecting the presence of a substance on a surface that differs from system 3000 in that system 3010 includes another alternate distal oral insertion portion 360 that includes the brush 352 with 352 with bristles 354 mounted on brush base 356, and as illustrated in FIG. 17 as viewed looking towards the brush base 356 and the upper tips of the bristles 354. As best illustrated in FIG. 19, each extending at an angle β with respect to the horizontal upper surface 356' of brush base 356 are distal probe tips 3212 and 3222 which enable multiple fluid flows to be directed at angle β towards the surface of interest such as surfaces 31 and 33 in FIGS. 2 and 7. In a similar manner, alternate or additional positions for distal probe tips 3212 and 3222 are illustrated by the dotted lines in the vicinity of the proximal end of the brush base 356 in FIG. 17.

The distal oral insertion portions 350 and 360 illustrated in FIGS. 14-16 and FIGS. 17-19 may be utilized for either: (a) the first method of detecting the presence of a substance on a surface which includes the measurement of bubble release from a tip (by pressure and/or pressure variations and/or bubble size and/or bubble release rate), or (b) for the second method of detecting the presence of a substance on a surface which includes the passage of the second fluid such as a gas or a liquid through the distal tip based on measurement of a signal, correlating to a substance obstructing the passage of fluid through the open port of the distal tip.

Figure 20:
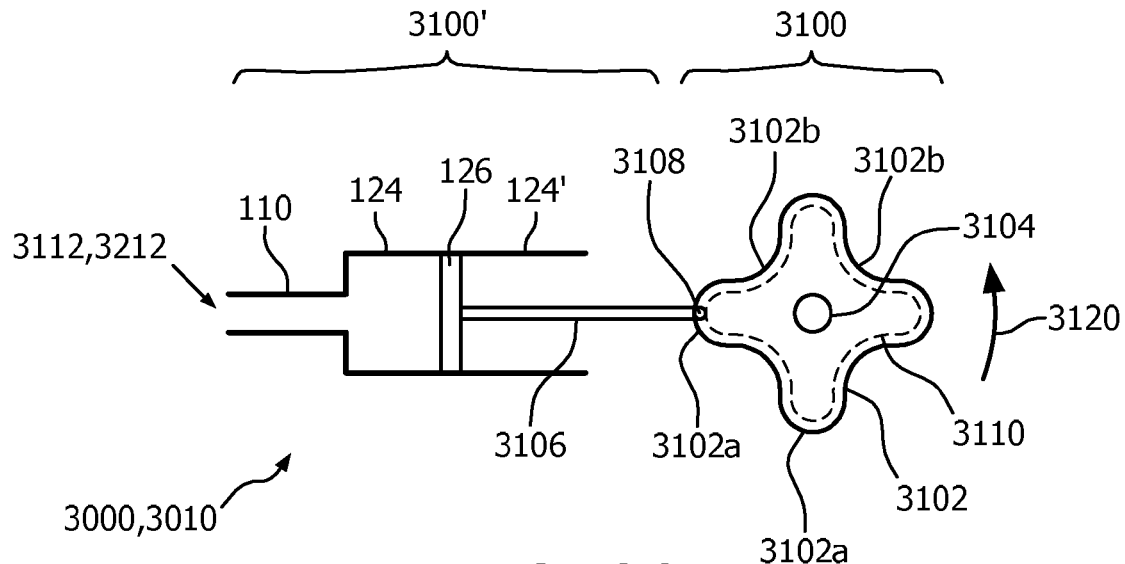
FIG. 20 illustrates one exemplary embodiment of the present disclosure of a system for detecting the presence of a substance on a surface wherein a stream probe operating apparatus includes a first stream probe.
Figure 21:
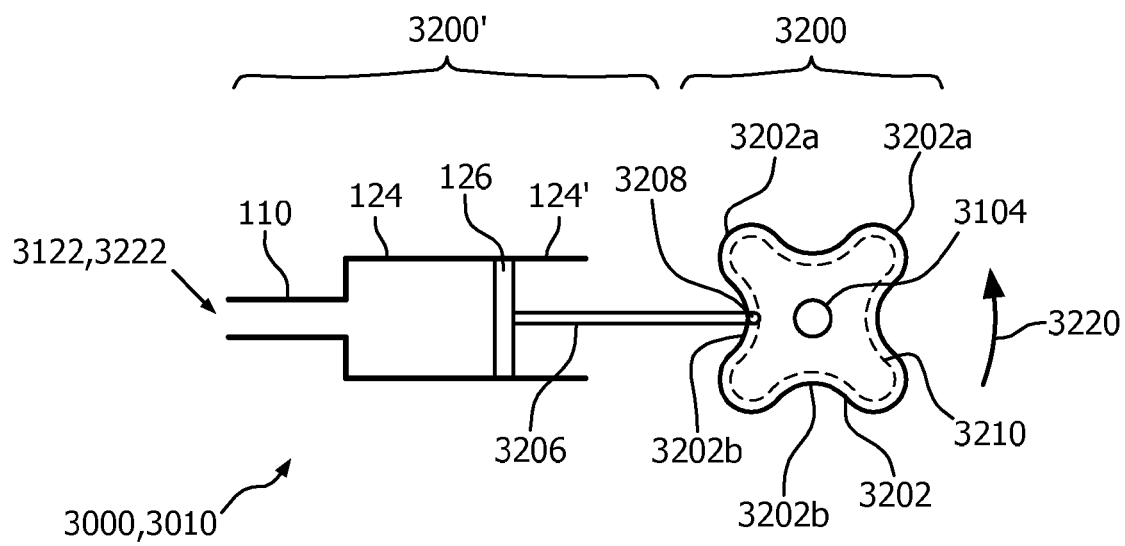
FIG. 21 illustrates the system of FIG. 20 wherein another stream probe operating apparatus includes a second stream probe.
Figure 22:
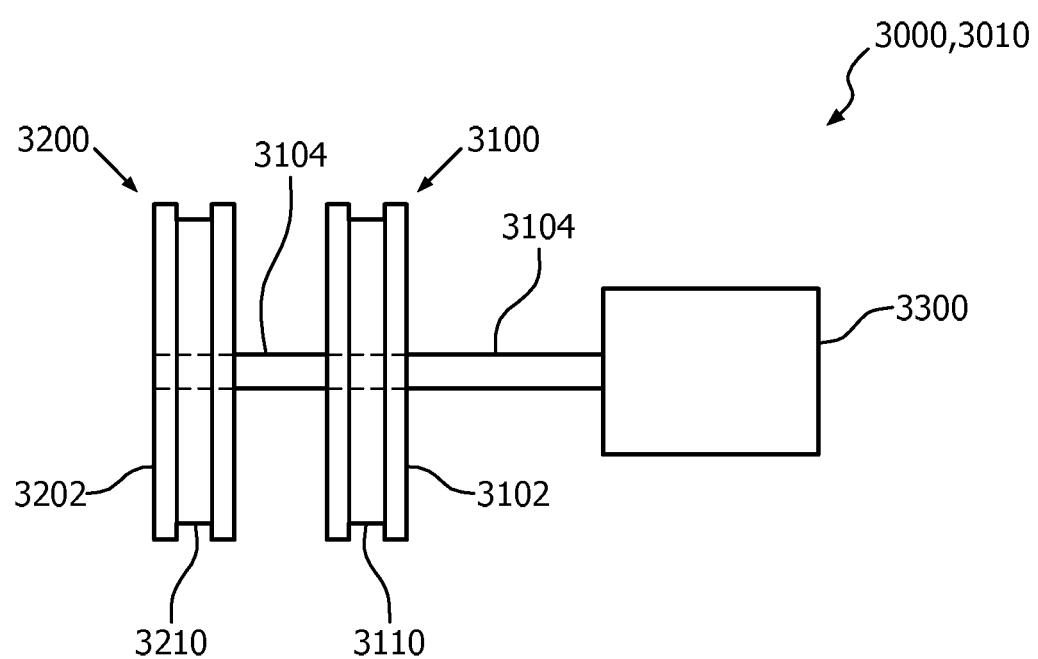
FIG. 22 illustrates the system of FIGS. 20 and 21 wherein a motor is operably connected to a common shaft that operates the stream probe operating apparatuses of FIGS. 20 and 21.

FIGS. 20-22 illustrate exemplary embodiments of the system 3000 or system 3010 that includes multiple stream probes and corresponding proximal pump portions that may be operated by a common rotating shaft and motor. More particularly, FIG. 20 illustrates a first stream probe operating apparatus 3100 that includes first stream probe 3100'. First stream probe 3100' is identical to the stream probe 100' described above with respect to FIG. 4B and may include the proximal pump portion 124 and plunger 126 and either the distal probe tip 3112 (see FIGS. 14-16) or the distal probe tip 3212 (see FIGS. 17-19). A rotary to linear motion operating member 3102, which may be a cam mechanism as illustrated, is in operable communication with the plunger 126 via a reciprocating shaft 3106 and a roller mechanism 3108 disposed on the proximal end of the shaft 3106.

The roller mechanism 3108 engages in a channel 3110 defining a path on the periphery of the cam mechanism 3102. The channel 3110 extends along the path to include cam peaks 3102a and cam troughs 3102b. The cam mechanism 3102 is mounted on and rotated by a common shaft 3104, in a direction such as the counterclockwise direction illustrated by arrow 3120. As the cam mechanism 3102 rotates, a reciprocating linear motion is imparted to the shaft 3106 as the roller mechanism 3108 is intermittently pushed by the peaks 3102a or pulled into the troughs 3102b. Thereby, a reciprocating linear motion is imparted to the plunger 126, pressure is generated in the stream probe 3100', and fluid flow passes through the distal tips 3112 or 3212. Those skilled in the art will understand that the path defined by the channel 3110 may be designed to impart a generally constant velocity to the plunger 126. Alternatively, the path defined by the channel 3110 may be designed to impart a generally constant pressure in the proximal pump portion 124. The plunger 126 is at a position distally away from the proximal end 124' of the proximal plunger portion 124 since the roller mechanism 3108 is at a peak 3102a.

FIG. 21 illustrates a second stream probe operating apparatus 3200 that includes second stream probe 3200'. Second stream probe 3200' is also identical to the stream probe 100' described above with respect to FIG. 4B and may include the proximal pump portion 124 and plunger 126 and either the distal probe tip 3122 (see FIGS. 14-16) or the distal probe tip 3222 (see FIGS. 17-19). Again, a rotary to linear motion operating member 3202, which may be a cam mechanism as illustrated, is in operable communication with the plunger 126 via a reciprocating shaft 3206 and a roller mechanism 3208 disposed on the proximal end of the shaft 3206.

Similarly, the roller mechanism 3208 engages in a channel 3210 defining a path on the periphery of the cam mechanism 3202. The channel 3210 extends along the path to include cam peaks 3202a and cam troughs 3202b. The cam mechanism 3202 is mounted on and rotated by a common shaft 3204, in a direction such as the counterclockwise direction illustrated by arrow 3220. As the cam mechanism 3202 rotates, a reciprocating linear motion is imparted to the shaft 3206 as the roller mechanism 3208 is intermittently pushed by the peaks 3202a or pulled into the troughs 3202b. Thereby, a reciprocating linear motion is also imparted to the plunger 126, pressure is generated in the stream probe 3200', and fluid flow passes through the distal tips 3122 or 3222. Again, those skilled in the art will understand that the path defined by the channel 3210 may be designed to impart a generally constant velocity to the plunger 126. Again, alternatively, the path defined by the channel 3110 may be designed to impart a generally constant pressure in the proximal pump portion 124. In contrast to first stream probe operating apparatus 3100, the plunger 126 is at a position at the proximal end 124' of the proximal plunger portion 124 since the roller mechanism 3208 is now at a trough 3202b.

FIG. 22 illustrates a motor 3300 that is operably connected to the common shaft 3104 such that the first rotary to linear motion operating member 3102 of stream probe operating apparatus 3100 is mounted proximally on the common shaft 3104 with respect to the motor 3300 while the second rotary to linear motion operating member 3202 of stream probe operating apparatus 3200 is mounted distally on the common shaft 3104 with respect to the motor 3300. Those skilled in the art will recognize that rotation of the common shaft 3104 by the motor 3300 causes the multiple stream probe operation as described above with respect to FIGS. 20 and 21. The motor 3300 is supplied electrical power by a power supply 270 mounted on proximal body portion 210 (see FIG. 10) such as a battery or ultracapacitor or alternatively a connection to an external power source or other suitable means (not shown).

Those skilled in the art will recognize that either stream probe operating apparatus 3100 or stream probe operating apparatus 3200 may operate the single air stream probe 1100 with multiple distal probe tips 3112 and 3122 described above with respect to FIG. 13 or the multiple distal probe tips 3212 and 3222 described above with respect to FIGS. 17-19.

Those skilled in the art will recognize that the stream operating apparatuses 3100 and 3200 described with respect to FIGS. 20-22 are merely examples of apparatuses which may be employed to effect the desired operation. For example, those skilled in the art will recognize that stream probe 100" and its associated components may replace the plunger 126 and either rotary to linear motion operating member 3102 or rotary to linear motion operating member 3202 or both and motor 3300 may be replaced by the diaphragm pump 150 that includes flexible or compressible diaphragm 158 as described above with respect to FIG. 4C.

The motor 3300 is in electrical communication with the controller 225 which controls the motor operation based on the signals received by the detector electronics 220. In addition to the alarm 226, the screen 125, the base station 228 and the smart phone 229 described above with respect to FIG. 10, in conjunction with FIG. 10, signaling to the user that plaque has been detected may include the controller 225 programmed to change the toothbrush drive mode by varying the operation of the motor 3300 to increase the brushing intensity either in frequency or in amplitude, or both, when plaque is detected. The increase in amplitude and/or frequency both signalling to the user to continue brushing in that area, and to improve effectiveness of removal. Alternatively, the controller 225 may be programmed to create a distinct sensation in mouth that the user can distinguish from regular brushing, for example by modulating the drive train to signal that plaque has been located.

A discussion will now be made with reference to FIGS. 23-29 regarding providing structural configurations to the stream probe tips or distal tips of the distal probe portions of the various embodiments described herein above for preventing blockage or obstruction of the passage of fluid through the open ports of the distal tips, such as distal tips 112, 112'. The various structural configurations also prevent false positives by ensuring that on a flat surface a flow escapes from the distal tips.

False positives can occur under several scenarios. For example, when approaching a teeth surface with a stream probe according to the present disclosure and, after making contact with the surface, a force is applied on the stream probe causing a pressure increase to occur, especially at a perpendicular positioning of the probe with respect to the clean surface. This pressure increase may be interpreted as plaque present on this location, even though the surface is clean. This means a false positive is generated.

Figure 23:
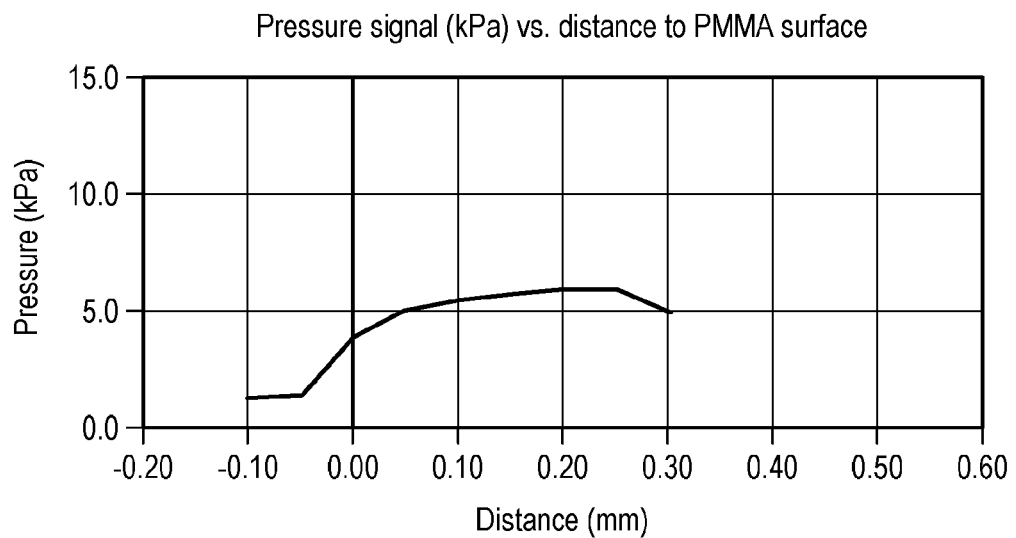
FIG. 23 is a graph illustrating pressure versus distance and showing a false positive measurement.

An example of such a false positive measurement is shown in FIG. 23, where the distance of the stream probe, being perpendicular to a dental surface, is varied. A negative distance in FIG. 23 means that the stream probe does not make contact with the PMMA surface. A positive distance means that the distance is further reduced and hence, by the flexibility in the tubing, the force on the stream probe is increased. A pressure increase is clearly observed when the probe is in contact with the PMMA surface. This pressure increase may be in the same order of magnitude or larger than the pressure increase from a dental plaque layer. Thus, a false positive will be generated. Reducing the distance even further results in bending of the stream probe and consequently, the air can more freely escape again.

According to the present disclosure, the structural configuration includes providing predefined shapes to the distal tips of the stream probes which overcomes false positives and/or prevents blocking of the open ports. False positives are prevented by ensuring that on a flat surface a flow always escapes from the distal tip. According to embodiments discussed herein below, due to the various shapes of the distal tip, the flow always escapes from the distal tip and it is independent of the angular orientation of the distal tip on the surface. This is advantageous because users significantly change the orientation of the distal tip when brushing the teeth.

The shape of the distal tip also prevents, as mentioned above, blockage or obstruction of the passage of fluid through the open port of the distal tip. The shape of the distal tip enables particles stuck or obstructing the open port of the distal tip to be easily released so that permanent blocking with not occur. These and other advantages of the present disclosure are realized by changing the profile or shape of the distal tip of the stream probe.

Figures 24A, 24B:
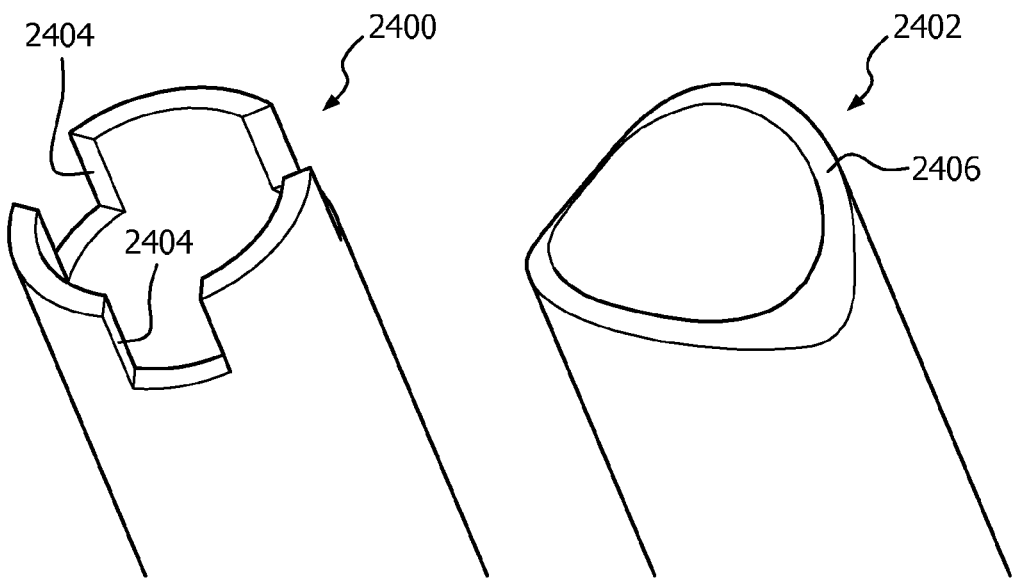
FIGS. 24A and 24B illustrate embodiments of structural configurations of the stream probe tip or distal tip according to the present disclosure, where
Figure 25:
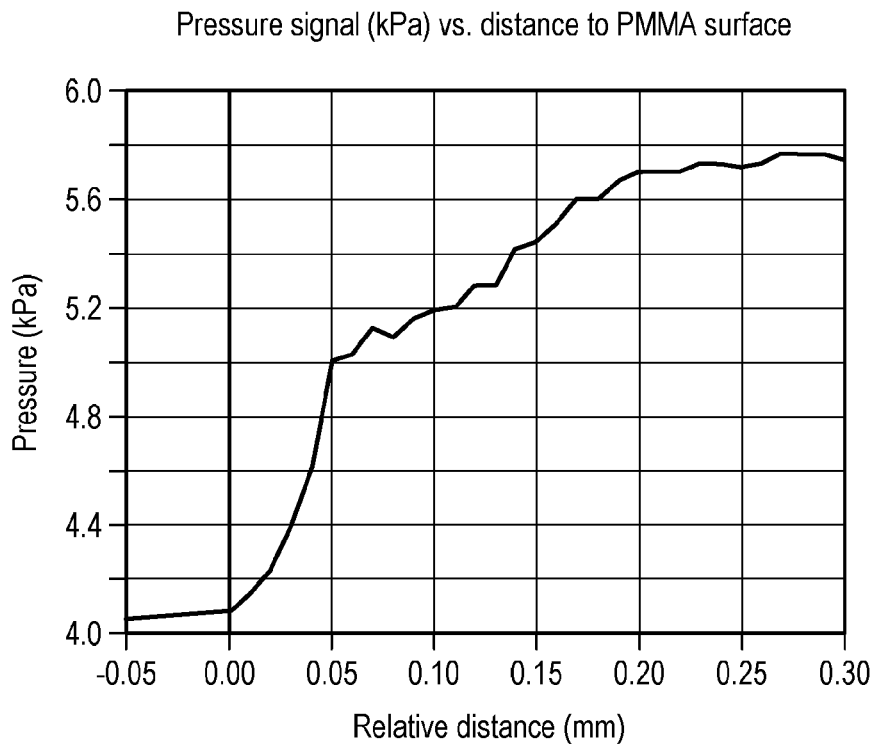
FIG. 25 is a graph illustrating pressure versus distance of a shaped tip probe to the PMMA surface according to the present disclosure, where negative values means no contact, zero just in contact, and positive values means increased contact force on the stream probe.

With reference to FIGS. 24A and 24B there are shown examples of probes 2400, 2402 having a castle-shape 2404 and a round shape 2406 distal tip (i.e., these shapes for the distal tips are structural configurations) to prevent false positive signals according to a first embodiment of the present disclosure. Though these tip shapes are suitable to prevent false positives, a risk is that the signal level from the plaque layers reduces as well. Therefore, it is favorable to limit the dimension(s) of the open area. In one preferred embodiment, the height of the opening should be below 100 microns in order to achieve sufficiently large signals from plaque layers on the PMMA surface. Using the tip shape shown by FIG. 24B, and measuring the pressure versus distance to the PMMA surface, there is shown in FIG. 25 a clear improvement in pressure versus distance of the shaped tip probe 2400 with respect to the unshaped tip (negative values means no contact with the PMMA surface, zero means just in contact with the PMMA surface, and positive values means increased contact force on the stream probe).

Figures 26, 27A, 27B:
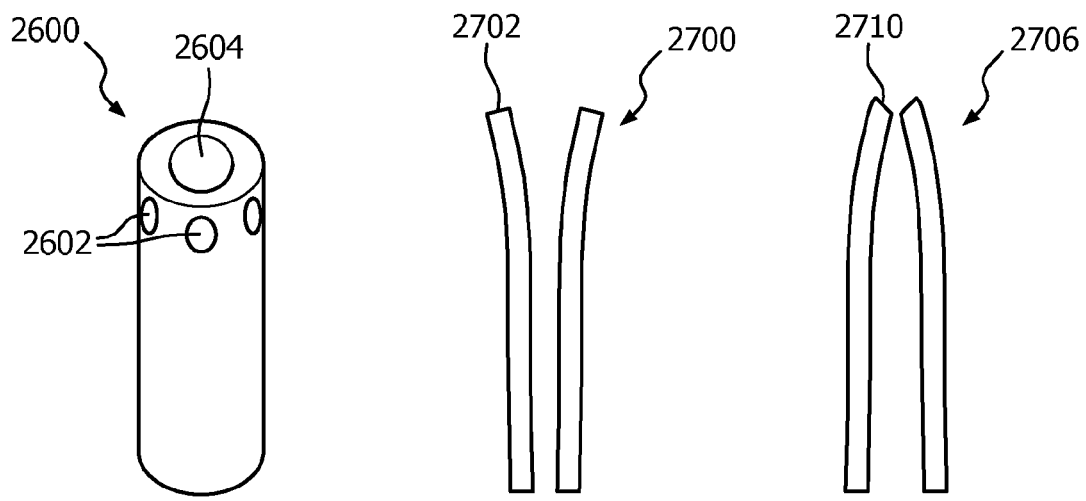
FIG. 26 illustrates an embodiment of a structural configuration of the stream probe tip or distal tip which includes a plurality of holes at a proximal location from an open port according to the present disclosure.
FIG. 27A illustrates an embodiment of another structural configuration of the distal tip according to the present disclosure which is a trumpet shape.
FIG. 27B illustrates an embodiment of still another structural configuration of the distal tip according to the present disclosure which is an inverse trumpet shape.

With reference to FIG. 26, according to a second embodiment of the present disclosure, false positive signals are prevented by providing a structural configuration to a stream probe 2600 which includes small holes 2602 near the distal tip of the probe 2600 or at a proximal location from an open port 2604. The holes 2602 are preferably within 100 microns of the distal tip of the probe 2600. An advantage of this embodiment is that it results in a stronger probe tip, which can be beneficial in case of wear issues.

With reference to a cross-sectional view as shown by FIG. 27A, according to a third embodiment of the present disclosure, the distal tip of a probe 2700 has a trumpet shape 2702 (i.e., structural configuration). That is, the inner diameter of the probe 2700 is larger at the end of the tube (at the distal tip) as compared to a position further away from the end. The tube appears to diverge at the distal tip. This shape prevents blocking of the distal tip of the probe 2700 by dental plaque or toothpaste.

In order to obtain large signals in case of a non-perpendicular tube orientation with respect to the tooth surface, it is beneficial to have a small tube diameter. Therefore, with respect to the embodiment shown by FIG. 27A, it is advantageous to apply a trumpet-like shape at the inside of the tube only, while the outside of the tube has a constant diameter throughout the length of the probe.

Another embodiment can be a tube having an inverse trumpet shape 2710 (i.e., structural configuration), where the distal tip of the probe 2706 converges rather than diverging. In this embodiment, the probe 2706 has a larger diameter further away from the distal tip as shown in the cross-sectional view of FIG. 27B. The inverse trumpet shape 2710 causes a pressure drop and achieves small tip dimensions in combination with low pressure drop/large diameter tube. The distal tips of the various embodiments can be made e.g. by heating Teflon® material and stretching it locally, resulting in the desired tip shape, such as the trumpet shape or the inverse trumpet shape.

With reference to FIG. 28, there is shown a cross-section of a fourth embodiment of the present disclosure which includes a rounded wall 2802 (i.e., structural configuration) at the distal tip or end of probe tube 2800.

With reference to FIG. 29, there is shown a cross-section of a fifth embodiment of the present disclosure, where the probe tube 2900 contains one or more bumper elements 2902 (i.e., structural configuration(s)) that extend outwardly, and thereby, prevent complete blocking of the fluid outlet or distal port when the distal tip might perpendicularly touch the tooth surface. The bumper element(s) 2902 can be situated in the center of the probe tube 2900 as shown by FIG. 29.

Other embodiments of structural configurations are contemplated herein, including combining two or more of the five embodiments discussed herein above. For example, a combination of the tip shapes of the first two embodiments with the third and fourth embodiments can be made. The new combined embodiment would be suitable for preventing both false positives and blocking of the distal tip.

A discussion will now be made with reference to FIG. 30 regarding providing structural configurations to the distal tips of the distal probe portions of the various embodiments described herein above for preventing wear of the distal tips, such as distal tips 112, 112'. The various structural configurations also prevent false positives by ensuring that on a flat surface a flow escapes from the distal tips.

According to the present disclosure, the stream probe tip or distal tip of the distal probe portion, such as distal probe portion (110), may include a structural configuration having a wear profile which is non-uniform around the circumference of the open port. The non-uniform wear profile ensures that the distal tip maintains its shape to a sufficient extent over a longer period of time.

As shown by FIG. 30, according to the present disclosure, the distal tip 3000 of a stream probe 3002 includes a non-uniform wear profile 3004 having at least two zones 3006, 3008 with different wear characteristics during brushing. The differential wear ensures a longer lifetime for the tube 3010. Also, since the tip profile maintains its shape to a sufficient extent, its differential wear design overcomes the false positive blocking of the plaque detection probe 3002 on clean teeth during normal use of the brush head with the probe 3002.

According to the present disclosure, the zones 3006, 3008 with different wear characteristics are alternatively placed over the circumference of the tube 3010, e.g., yielding high wear, low wear, high wear, and low wear. According to this design, a tip shape like the one shown by FIG. 30 can be maintained over the lifetime of the tube 3010.

Figures 34, 35:
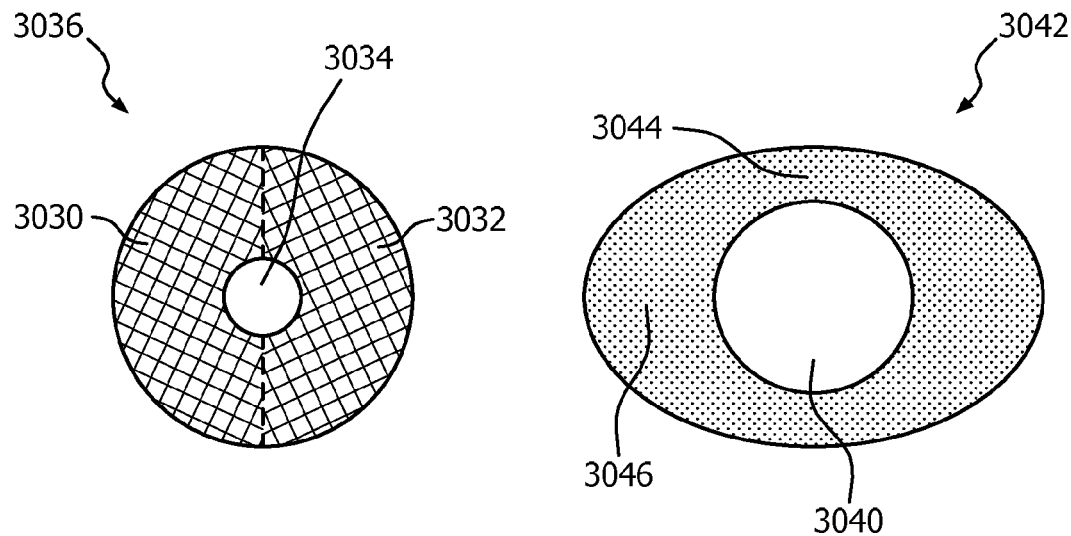
FIG. 34 illustrates a cross-section of a stream probe tip or distal tip according to another embodiment of the present disclosure in which a material is ordered or oriented differently around the distal tip circumference to provide a non-uniform wear profile for the distal tip.
FIG. 35 illustrates a cross-section of a stream probe tip or distal tip according to still another embodiment of the present disclosure in which different wall thickness dimensions around the circumference provide a non-uniform wear profile.

The non-uniform wear profile 3004 is achieved in several ways. In a first embodiment according to the present disclosure, each of the at least two zones 3006, 3008 includes a different material than the other zone, with the two materials having different wear characteristics. In a second embodiment according to the present disclosure, the at least two zones 3006, 3008 have the same material but the material is processed in a manner that the wear properties are non-uniform around the distal tip circumference. Also, according to a third embodiment of the present disclosure, the at least two zones 3006, 3008 are made of the same material but the material is ordered or oriented differently around the distal tip circumference as shown by FIG. 34. This causes the material to have asymmetric wear around the tip circumference caused by the ordering of the material in relation to the linear motion of the tube 3010 during brushing. A fourth embodiment includes using a tube with different wall thickness dimensions around the circumference as shown by FIG. 35.

The four above mentioned embodiments according to the present disclosure will now be further described. In the first embodiment, the non-uniform wear profile 3004 around the circumference of the distal tip 3000 is realized by providing at least two different materials with different wear characteristics at the distal tip 3000 in contact with the teeth.

As an example, the distal tip 3000 with the suitable tip profile as shown in FIG. 30 is realized using a slower wearing material at the two positions around the tip circumference where the tip profile is highest and a faster wearing material at the two positions around the tip circumference where the tip profile is lowest. In this manner, the excess wear at the raised part of the tip profile (induced by the locally higher contact pressure) will be offset by the faster wear rate at the lower part of the tip profile (despite of the locally lower contact pressure). As a result, the desired tip profile will—to at least a certain extent—be maintained during the lifetime of the tube 3010.

The difference in wear can be achieved by choosing a difference in hardness of the two materials. Also, a difference in brittleness will result in a difference in wear. Differential wear may involve the use of, for example, materials with different crystallinity, molecular weight, molecular composition, and cross-linking.

Furthermore, differential wear may be generated by differential additives, e.g., fibrous material, nanoparticles, or microparticles. As illustrated by FIG. 31, differential wear may be generated by embedding into the distal tip 3012 a first material 3014 into a second material 3016. For example, the first material can be a filamentous material that is linearly ordered within the matrix of the tube material or second material.

One skilled in the art can appreciate that there can be other configurations with respect to the first embodiment to create a non-uniform wear profile for the stream probe tip or distal tip, such as more than two regions having different wear characteristics around the tip circumference; having more than two different materials with different wear properties; the addition of at least one layer of a second material 3018 at at least one strategic position around a tube 3020 of a single material 3021 (second material 3018 placed over portions of the single material 3021) (see FIG. 32); the addition of a layer of a second material 3022 placed entirely around a tube 3024 of a single material 3025 (second material 3022 placed entirely over the single material 3025) (see FIG. 33); etc.

In the second embodiment according to the present disclosure, the at least two zones 3006, 3008 shown by FIG. 30 have the same material but the material is processed in a manner that the wear properties or characteristics are non-uniform or different around the distal tip circumference.

For example, zones 3006 of FIG. 30 can be realized using a first material processed in a manner in which the wear characteristics are slower than zone 3008. The first material may be doped with another material which is known to cause the first material to wear slower than without doping. Zones 3008 can be realized using a second material processed in a manner in which the wear characteristics are faster. The second material may be doped with another material which is known to cause the second material to wear faster than without doping. It is also contemplated that the first and second materials are the same material but are doped with different materials/substances to affect their strength or hardness.

Another suitable processing method leading to materials with slower wearing characteristics when brushing a tooth are increasing the surface hardness of the material by ion implanting. Differential wear may also be generated by radiation treatment that changes the distal tip and tube material in a non-rotationally symmetric way, e.g., using radiation to cause photophysical or photochemical effects on the material to make it wear faster than without the radiation treatment. Differential wear may also be generated by adding one or more additional layers of another material to strategic positions around the tube as described above with reference to FIGS. 32 and 33. According to the second embodiment of the present disclosure, the excess wear at the raised part or high point of the tip profile (zones 3006 in FIG. 30) (induced by the locally higher contact pressure) will be offset by the faster wear rate at the lower part or low point of the tip profile (zones 3008 in FIG. 30) (despite of the locally lower contact pressure). As a result, the desired tip profile will—to at least a certain extent—be maintained for a longer period of time.

In a third embodiment according to the present disclosure, the at least two zones 3006, 3008 shown by FIG. 30 are made of the same material but the material is ordered or oriented differently around the distal tip circumference of the opening 3034 of the tube 3036 as shown by FIG. 34 to create a non-uniform wear profile. The ordering causes the material to have asymmetric wear around the tip circumference in relation to the linear motion of the tube 3010 during brushing. FIG. 34 illustrates the ordering of the material being different around the distal tip circumference of the opening 3034 of the tube 3036 by the two different orientations of the hash lines. A first set of hash lines 3030 are oriented in a different direction than a second set of hash lines 3032.

The material can be crystalline ceramic, ordered or stretched polymer, etc. with asymmetric wear around the tip circumference of the opening 3034 caused by the ordering of the material in relation to the linear motion of the tube 3036 during brushing.

As an example, the tip with a suitable tip profile as shown in FIG. 34 is realized using an ordered material which—due to its orientation and the direction of brushing—has slower wearing characteristics at the two positions around the tip circumference as shown by FIG. 30 where the tip profile is highest and a material—due to its orientation and the direction of brushing—exhibits faster wearing characteristics at the two positions around the tip circumference where the tip profile is lowest as shown by FIG. 30.

In this manner, the excess wear at the raised part or high point of the tip profile (zones 3006 in FIG. 30) (induced by the locally higher contact pressure) will be offset by the faster wear rate at the lower part or low point of the tip profile (zones 3008 in FIG. 30) (despite of the locally lower contact pressure). As a result, the desired tip profile will—to at least a certain extent—be maintained for a longer period of time.

It is contemplated that for the third embodiment two or more different materials can be used and ordered or oriented differently around the distal tip circumference to create the non-uniform wear profile.

A fourth embodiment according to the present disclosure includes using a tube 3042 with different wall thickness dimensions (i.e., non-uniform wall thickness) over the circumference of an opening 3040 of the tube 3042 as shown by FIG. 35 to create a non-uniform wear profile. At the thin wall positions or zones 3044, the tip will wear more easily than the thick wall positions or zones 3046, and consequently the shape of the distal tip and tube 3042 is substantially remained over a longer period of time.

The thickness profile may be generated, for example, by injection molding, mechanical deformation, mechanical removal of material to generate the thin wall zones 3044, and/or the addition of material to generate the thick wall zones 3046.

According to further aspects of the present disclosure, the distal probe portions (110) of the stream probe of the various embodiments described herein have structural configurations which include two or multiple components or segments to improve performance and reliability. Table 1 below shows the direction for the optimization of hardness, vertical stiffness, bending stiffness, and diameter for all the requirements of the stream probe, such as stream probe 10.

TABLE 1

|  | Hardness | Vertical stiffness | Bending stiffness | Diameter |
| --- | --- | --- | --- | --- |
| Plaque detection | Hard | Sufficiently high | Sufficiently high | Small |
| Wear | Hard | Low | Low | Large |
| Pokiness | Soft | Low | Low | Large |
| Damage dentine/gum | Soft | Low | Low | Large |
| False blocking | Hard | Low | Low | Large |
| Pressure drop | NA | NA | NA | Large |
| Blockage prevention by particles | Hard | Low | Low | Large |

It is clearly visible from Table 1 that the various requirements for the stream probe 10 there are different optimizations of hardness, vertical stiffness, bending stiffness, and diameter. Accordingly, a single tubing system may not be optimal for all requirements of the stream probe 10.

According to the present disclosure, by combining a hard, wear resistant material with relatively small dimensions at the tip of the plaque detection stream probe 10 with a larger diameter more flexible tube at the bottom of or at a distance from the plaque detection stream probe 10 optimizes the performance of the plaque detection systems and apparatuses.

Figure 36:
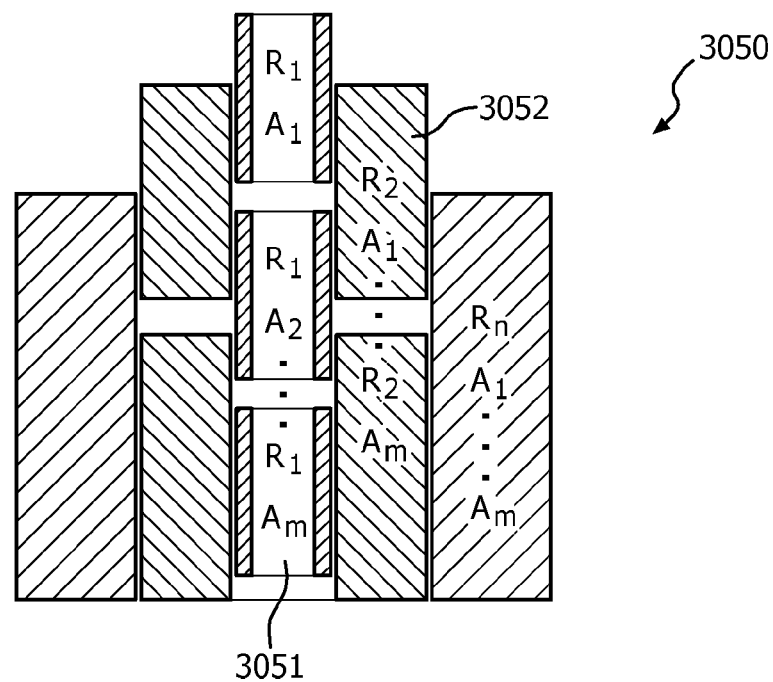
FIG. 36 illustrates a cross-sectional view of an exemplary multiple-component tube system according to the present disclosure.

FIG. 36 is a cross-sectional view of an exemplary multiple-component tube system according to the present disclosure designated generally by reference numeral 3050. The tube system 3050, shown by FIG. 36, contains 2 . . . n layers 3052 of different tubing materials (in the radial or "R" direction) of the distal probe portion combined with 1 . . . m number of tubes or components 3054 in the axial direction (axial or "A" direction) for each layer of tubing 3052. Also within this axial direction, the materials might be different from each other with different characteristics. There can also be a certain distance of separation between the adjacent tubes 3054 as shown by FIG. 36 to optimize for flexibility of the whole tubing system 3050.

Figure 37:
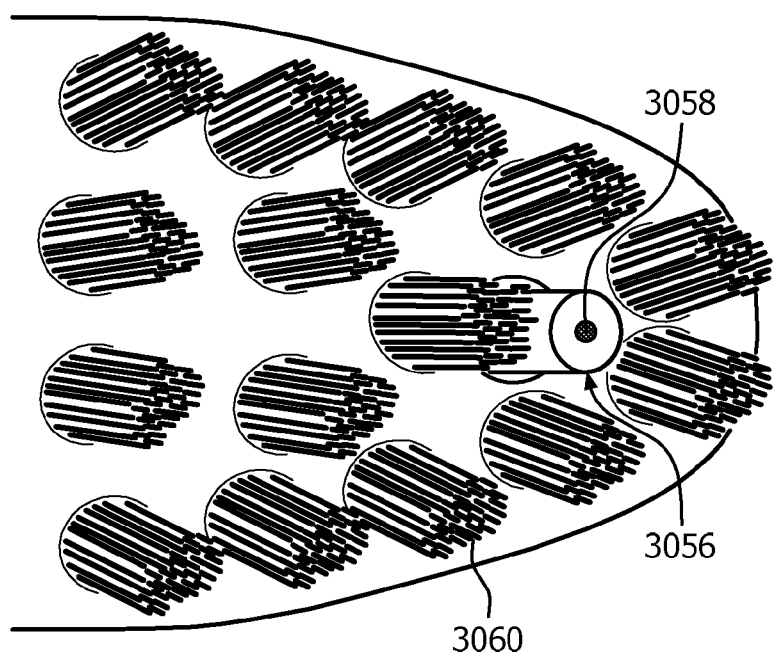
FIG. 37 illustrates a two-component tube system according to an embodiment of the present disclosure.

A first embodiment for optimizing probes having a multiple-component tube system as FIG. 36 is shown by FIG. 37. FIG. 37 illustrates a two-component tube system 3056 having a tip 3058 and a second tube 3060 with a larger diameter. The tip material should be hard material (but not harder than the dentine) which has good properties for wear. For example, PEEK material can be used. Dimensions are below 500 micron for the outer diameter and preferably below 350 micron for the outer diameter. An example of a tip length is 4 mm, where, for example, 2.5 mm is sticking into the larger tubing.

The tubing material below the tip 3058 should be flexible and have a larger inner diameter as compared to the tip to ensure a low pressure drop. Suitable materials for the tubing material below the tip 3058 are, for example, Teflon®, polyurethane, and Silastic®. The length of the tube may be, for example, 7 mm. Hence, according to the present disclosure, by adjusting the diameter, wall thickness and material properties of the tubing, the desired stiffness (both vertically and horizontally) can be tuned. In this manner, a customized solution can be made to obtain a reliable, user-friendly and wear resistant plaque detection probe/assembly.

Figures 38, 39:
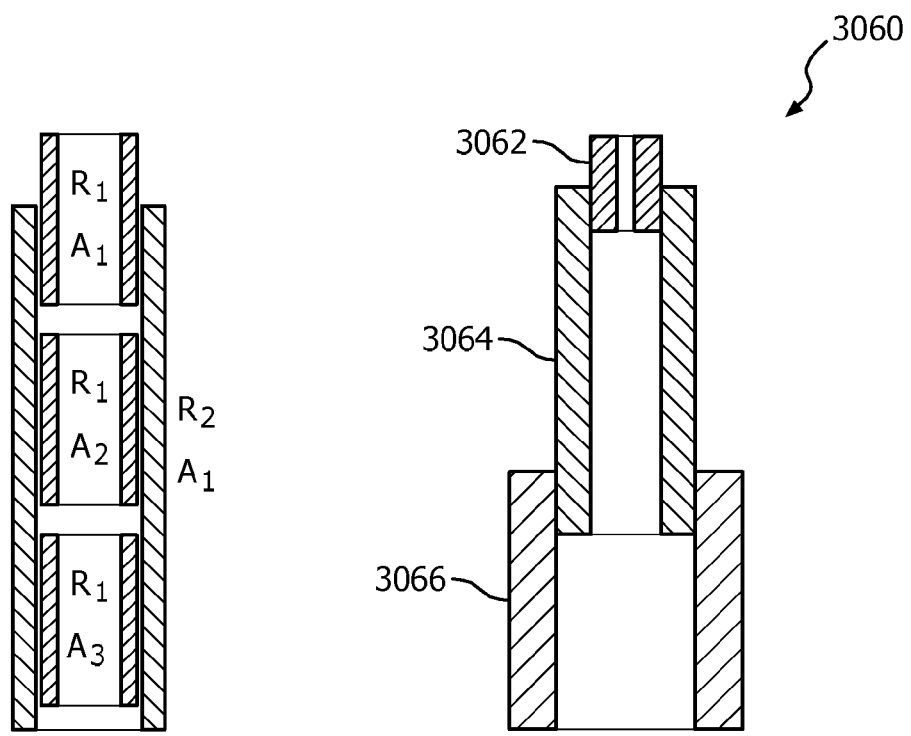
FIG. 38 illustrates a cross-sectional view of another exemplary embodiment of a tube having multiple components according to the present disclosure.
FIG. 39 illustrates a cross-sectional view of an exemplary embodiment of a probe with three tubing materials according to the present disclosure.

FIG. 38 is a cross-sectional view of another exemplary embodiment of a tube having multiple components for adjusting flexibility. In the embodiment shown by FIG. 38, there is a hard and wear resistant tubing material R1 which addresses the requirements of probe wear, plaque detection and stiffness of the construction. Material R2 can be more flexible than material R1 to address the flexibility needed for the other requirements shown, for example, in Table 1.

FIG. 39 is a cross-sectional view of another exemplary embodiment of a probe 3060 with three tubing materials. The probe 3060 includes a tip of hard material 3062, a flexible tube with a larger diameter 3064, and another tube 3066 with a non-stiff material with an even larger diameter. By controlling the length of the tubes 3064, 3066, the stiffness of the probe 3060 can be tuned to the desired value.

Figure 40:
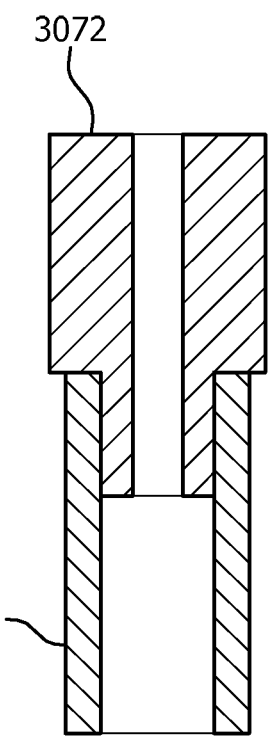
FIG. 40 illustrates a cross-sectional view of another exemplary embodiment of a probe according to the present disclosure.

FIG. 40 is a cross-sectional view of another exemplary embodiment of a probe 3068 where the outer and inner diameters of subsequent segments or components 3070, 3072 may modulate or change. FIG. 40 shows modulation of the outer diameter along the length of the tube segment 3072.

Figure 41:
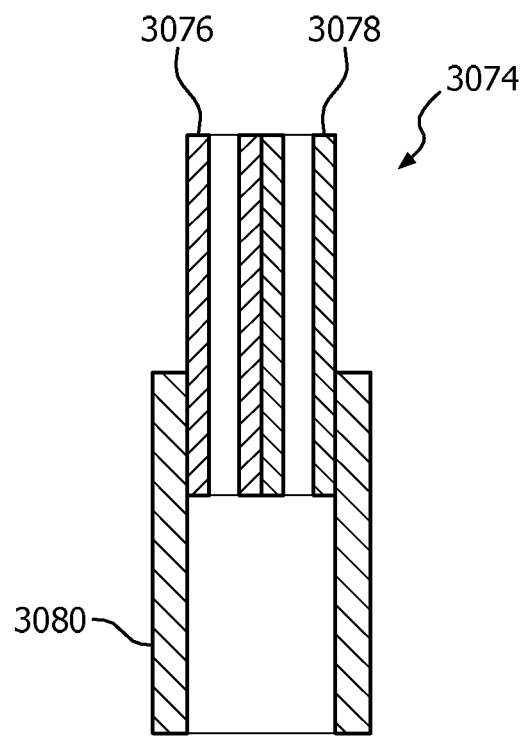
FIG. 41 illustrates a cross-sectional view of still another exemplary embodiment of a probe according to the present disclosure.

FIG. 41 is a cross-sectional view of another exemplary embodiment of a probe 3074. The segments or components of tubes 3076, 3078, 3080 are assembled in non-coaxial arrangements. As shown by FIG. 41, two tubes 3076, 3078 with similar diameters are inserted into a tube 3080 with a larger diameter.

In the multiple-component embodiments discussed herein, the components may have non-circular cross-sections, e.g., an oval cross-section or a rectangular cross-section. Other multiple-component embodiments having different configurations than those configurations described herein can be implemented according to the teachings of the present disclosure.

According to the present disclosure, the supply of air bubbles to a tooth brush may also improve the plaque removal rate of the brushing. One possible mechanism is that (i) air bubbles will stick to spots of clean enamel, (ii) brushing brings a bubble into motion, and thereby also the air/water interface of the bubble, and (iii) when the bubble edge contacts plaque material, the edge will tend to peel the plaque material off the enamel, because the plaque material is very hydrophilic and therefore prefers to stay in the aqueous solution. Another possible mechanism is that the presence of bubbles can improve local mixing and shear forces in the fluid, thereby increasing the plaque removal rate. It should be noted that other exemplary embodiments of the methods of detection of a substance on a surface as described herein may include monitoring the first derivative of the signals, AC (alternating current) modulation, and utilization of a sensor for gum detection.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention may be implemented by means of hardware comprising several distinct elements, and/or by means of a suitably programmed processor. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. An electric toothbrush comprising:
   an oral insertion portion;
   a body portion containing gas supply apparatus and detection electronics;
   at least one parameter sensor in electrical communication with the detection electronics for measuring a change in a parameter;
   a stream probe detection apparatus configured to detect the presence of a substance on a dental surface, the apparatus comprising:
   a distal probe portion in the oral insertion portion configured to be immersed in a first fluid,
   the distal probe portion defining a distal tip having an open port to enable the passage of a gas therethrough;
   the at least one parameter sensor configured such that passage of the gas through the distal tip enables detection of a substance that may be present on the dental surface based on measurement by the detection electronics of a change in the pressure signal detected by the at least one parameter sensor, correlating to a substance at least partially obstructing the passage of fluid through the open port of the distal tip, the detection electronics configured to determine, based on the change in the pressure signal, whether the substance present on the dental surface is more hydrophilic than the dental surface, wherein the distal tip has a structural configuration for preventing blocking of said open port by the substance,
   wherein the detection electronics, based on the change in pressure signal, is configured to determine if the substance present on the dental surface is plaque.

2. The electric toothbrush according to claim 1, wherein the structural configuration of the distal tip is one of a castle-shape, a round-shape, a trumpet shape, an inverse trumpet shape or chamfered.

3. The electric toothbrush according to claim 1, wherein the structural configuration of the distal tip includes a plurality of holes at a proximal location from said open port.

4. The electric toothbrush according to claim 1, wherein the structural configuration of the distal tip includes at least one bumper element extending from the distal tip.

5. A method for detecting the presence of a substance on a dental surface, the method comprising:
   immersing in a first fluid a distal probe portion, the distal probe portion defining a distal tip having an open port to enable the passage of a gas therethrough, and
   due to passage of the gas through the distal tip, detecting by means of a parameter sensor a substance that may be present on the dental surface based on measurement by detection electronics of a change in a pressure signal detected by the parameter sensor, correlating to a substance at least partially obstructing the passage of fluid through the open port of the distal tip, and determining by means of the detection electronics, based on the change in the pressure signal, whether the substance present on the dental surface is more hydrophilic than the dental surface, wherein the detection electronics, based on the change in pressure signal, determines if the substance present on the dental surface is plaque.

6. The electric toothbrush according to claim 1 wherein the detection electronics is configured to determine if the level of plaque exceeds a predetermined level of plaque.

7. The electric toothbrush according to claim 1 wherein the detection electronics is configured to provide feedback to a user to clean the dental surface in the area where the plaque level exceeded the predetermined level of plaque.

8. The method according to claim 5, wherein if the detection electronics determines that the level of plaque exceeds a predetermined maximum permissible level of plaque, the detection electronics provides feedback to a user to clean the dental surface in the area where the plaque level exceeded the predetermined maximum permissible level of plaque.

9. The method according to claim 5 wherein if the detection electronics determine that the substance present on the dental surface is plaque, the detection electronics determines if the level of plaque exceeds a predetermined maximum permissible level of plaque.

\* \* \* \* \*